United States Patent
Miyata

(10) Patent No.: US 7,368,251 B2
(45) Date of Patent: *May 6, 2008

(54) MEGSIN PROTEIN

(75) Inventor: Toshio Miyata, 4-2-3-101, Higashinaruse, Isehara-shi, Kanagawa (JP) 259-1117

(73) Assignees: Tokai University Educational System, Tokyo (JP); Toshio Miyata, Kanagawa (JP); Kiyoshi Kurokawa, Tokyo (JP)

( * ) Notice: Subject to any disclaimer, the term of this patent is extended or adjusted under 35 U.S.C. 154(b) by 347 days.

This patent is subject to a terminal disclaimer.

(21) Appl. No.: 10/927,766

(22) Filed: Aug. 26, 2004

(65) Prior Publication Data

US 2005/0106628 A1    May 19, 2005

Related U.S. Application Data

(63) Continuation of application No. 09/508,997, filed as application No. PCT/JP98/04269 on Sep. 22, 1998, now abandoned.

(30) Foreign Application Priority Data

Sep. 22, 1997    (JP) .................................. 9-275302

(51) Int. Cl.
- *G01N 33/53* (2006.01)
- *G01N 33/537* (2006.01)
- *G01N 33/566* (2006.01)

(52) U.S. Cl. ...................... 435/7.1; 435/7.8; 435/7.92; 436/501; 436/503

(58) Field of Classification Search ...................... None
See application file for complete search history.

(56) References Cited

U.S. PATENT DOCUMENTS 5,194,596 A * 3/1993 Tischer et al. .............. 530/399
5,350,836 A * 9/1994 Kopchick et al. ........... 530/399
5,831,030 A * 11/1998 Tsujimoto et al. ....... 530/387.9
7,026,126 B1 * 4/2006 Miyata ....................... 435/7.1

FOREIGN PATENT DOCUMENTS

| CA | 2366651 | 9/2000 |
|---|---|---|
| EP | 0 583 884 A1 | 2/1994 |
| JP | 6-313000 A | 11/1994 |

OTHER PUBLICATIONS

Vukicevic et al., 1996, PNAS USA 93:9021-9026.*
Choh, PNAS 77(6):3211-14, 1990.*
Skolnick et al., Trends in Biotech., 18(1):34-39, 2000.*
Sambrook, Molecular Cloning, 1989, 9.47-51 and 11.48-49.*
Konopka (Proc. Natl. Acad. Sci. (1986) 83:4049-4052.*
Miyata et al., *J. Am. Soc. Nephrol.*, 9:503A (1998).
Miyata et al., *J. Clin. Invest.*, 120:828-836 (1998).
Suzuki et al., *J. Am. Soc. Nephrol.*, 10:2606-2613 (1999).
Tsujimoto et al., *J. Biol. Chem.*, 272:15373-15380 (1997).
EMBL Accession No. D88575 (Jul. 6, 1998).
EMBL Accession No. EO8396 (Oct. 8, 1997).
Potempa et al., "The Serpin Superfamily of Proteinase Inhibitors: Structure, Function and Regulation" J. Biol. Chem., 269(23):15957-60 (Jun. 10, 1994).

* cited by examiner

Primary Examiner—Olga N. Chernyshev
(74) Attorney, Agent, or Firm—Karl Bozicevic; Bozicevic, Field & Francis LLP

(57) ABSTRACT

A gene expressed specifically in mesangial cells. A DNA expressed specifically in mesangial cells; a protein encoded by this DNA; an antibody binding to this protein, etc. These substances are indigenous to mesangial cells and, therefore, useful in, for example, identifying mesangial cells and detecting abnormalities in mesangial cells. Moreover, the above protein would be helpful for clarification of the functions of masangial cells and, in its turn, for clarification of the causes of diseases relating to masangial cells. This protein is expectedly applicable to the treatment and diagnosis of diseases relating to masangial cells.

1 Claim, 7 Drawing Sheets

```
M A S L A A A N A E F C F N L F R E M D    20
D N Q G N G N V F F S S L S L F A A L A    40
L V R L G A Q D D S L S Q I D K L L H V    60
N T A S G Y G N S S N S Q S G L Q S Q L    80
K R V F S D I N A S H K D Y D L S I V N   100
G L F A E K V Y G F H K D Y I E C A E K   120
L Y D A K V E R V D F T N H L E D T R R   140
N I N K W V E N E T H G K I K N V I G E   160
G G I S S S A V M V L V N A V Y F K G K   180
W Q S A F T K S E T I N C H F K S P K C   200
S G K A V A M M H Q E R K F N L S V I E   220
D P S M K I L E L R Y N G G I N M Y V L   240
L P E N D L S E I E N K L T F Q N L M E   260
W T N P R R M T S K Y V E V F F P Q F K   280
I E K N Y E M K Q Y L R A L G L K D I F   300
D E S K A D L S G I A S G G R L Y I S R   320
M M H K S Y I E V T E E G T E A T A A T   340
G S N I V E K Q L P Q S T L F R A D H P   360
F L F V I R K D D I I L F S G K V S C P   380
                              (SEQ ID NO:2)
```

FIG.1

| | | | | | | | | | | | | | | | | | | | | | | |
|---|---|---|---|---|---|---|---|---|---|---|---|---|---|---|---|---|---|---|---|---|---|---|
| 331-351 (SEQ ID NO:2) | megsin | E | E | G | T | E | A | T | A | A | T | G | S | N | I | V | E | K | Q | L | P | Q |
| SEQ ID NO:47 | SCC1 | E | E | G | A | E | A | A | A | A | T | A | V | V | G | F | G | S | S | P | T | S |
| SEQ ID NO:48 | ILEU | E | E | G | T | E | A | A | A | A | T | A | G | I | A | T | F | C | M | L | M | P |
| SEQ ID NO:49 | PAI-2 | E | E | G | T | E | A | A | A | G | T | G | G | V | M | T | G | R | T | G | H | G |
| SEQ ID NO:50 | OVA | E | A | G | R | E | V | V | G | S | A | E | A | G | V | D | A | A | S | V | S | - |

1 2 3 4 5 6 7 8 9

MEGSIN PROTEIN

TECHNICAL FIELD

The present invention belongs to the field of genetic engineering and specifically relates to a gene isolated from renal cells.

BACKGROUND ART

Sixty trillion various cells in vivo essentially comprise identical genomic DNA. For the normal physiological functions, the expression of these genes is strictly controlled by signals received by cell lines and cells. Therefore, elucidation of genes expressed specifically in each cell type is very important.

A mesangial cell plays a pivotal role in maintaining the structure and function of a glomerulus and is a target of disorders for each type of nephritis. For example, proliferation of mesangial cells and accumulation of extracellular mesangial matrix are thought to be the first step developing glomerulosclerosis in a patient suffering from various glomerular diseases such as chronic nephritis and diabetic nephritis. Therefore, identification of genes expressed specifically in mesangial cells and elucidation of its function are helpful for understanding biological characteristics of mesangial cells and the causes of diseases relating to mesangial cells, and in turn, treating or diagnosing diseases relating to mesangial cells.

Thy1 antigen is known as a marker for mesangial cells in rats. However, this gene is not specific to mesangial cells and is not expressed in human mesangial cells (Miyata T. et al., Immunology, 1989, 67: 531-533; and Miyata T. et al., Immunology, 1990, 69: 391-395). Mesangial cells are known to express α smooth muscle actin when activated, but this gene is also not specific to mesangial cells. Any genes expressed specifically in mesangial cells have not been reported.

DISCLOSURE OF THE INVENTION

An objective of the present invention is to isolate a gene expressed specifically in mesangial cells.

The current inventors isolated mRNA from in vitro cultures of human mesangial cells to construct a cDNA library of 3' side. Sequences of numerous clones were randomly determined from the cDNA library and compared with the known nucleotide sequences of cDNA clones of 3' side obtained from various organs and cells to determine the clones expressed specifically in mesangial cells. One clone which appeared the most frequently in the mesangial cells was selected, and its full length cDNA was isolated (the expression product was named as MEGSIN) by 5' RACE method to determine the whole nucleotide sequence and express the said cDNA in E.coli (SEQ ID NO: 1 and SEQ ID NO: 2 show the nucleotide sequence of human MEGSIN cDNA and the deduced amino acid sequence, respectively). The homology search in amino acid sequences with SwissProt data base revealed that MEGSIN belongs to SERPIN super family (R. Carrell et al., Trends Biochem Sci. 10, 20, 1985; R. Carrell et al., Cold Spring Harbor Symp. Quant. Biol. 52, 527, 1987; E. K. O. Kruithof et al., Blood 86, 4007, 1995, J. Potempa et al., J. Biol. Chem. 269, 15957, 1994; and E. Remold-O'Donnell FEBS Let. 315, 105, 1993). The topography detected by Northern blotting confirmed that the expression of MEGSIN was weak in human fibroblasts, smooth muscle cells, endothelial cells, and keratinocytes, and was specifically in mesangial cells. The comparison of MEGSIN expression level in renal tissues from the IgA nephropathy patients and the normal people revealed that the expression level of MEGSIN in the IgA nephropathy patients was significantly larger. Anti-MEGSIN polyclonal antibody and monoclonal antibody were prepared. In addition, the inventors confirmed the structures of mouse and rat MEGSIN homologues. The nucleotide sequences of cDNA of mouse MEGSIN and rat MEGSIN are shown in SEQ ID NO: 3 and SEQ ID NO: 5, respectively, and the deduced amino acid sequences for these are shown in SEQ ID NO: 4 and SEQ ID NO: 6, respectively.

The present invention specifically relates to the followings.

(1) A protein comprising the amino acid sequence of SEQ ID NO: 2, SEQ ID NO: 4, or SEQ ID NO: 6, or a protein comprising the amino acid sequence of SEQ ID NO: 2, SEQ ID NO: 4, or SEQ ID NO: 6 in which one or more amino acids are replaced, deleted, added, and/or inserted, and functionally equivalent to the protein comprising the amino acid sequence of SEQ ID NO: 2, SEQ ID NO: 4, or SEQ ID NO: 6

(2) The protein of (1), comprising an amino acid sequence selected from the group consisting of SEQ ID NO: 2, SEQ ID NO: 4, and SEQ ID NO: 6.

(3) A DNA encoding the protein of (1).

(4) The DNA of (3), comprising a nucleotide sequence selected from the group consisting of SEQ ID NO: 1, SEQ ID NO: 3, and SEQ ID NO: 5.

(5) A DNA hybridizing with a DNA comprising a nucleotide sequence selected from the group consisting of SEQ ID NO: 1, SEQ ID NO: 3, and SEQ ID NO: 5 under the stringent condition, and encoding the protein of (1) or the protein functionally equivalent thereto.

(6) A vector comprising the DNA of any one of (3), (4), and (5).

(7) A transformed cell expressiblly comprising the DNA of any one of (3), (4), and (5).

(8) A method for producing the protein of (1), the method comprising culturing the transformed cell of (7) and collecting an expression product of the DNA of any one of (3), (4), and (5).

(9) An antibody binding to the protein of (1).

(10) The antibody of (9), which recognizes an epitope of a protein comprising an amino acid sequence selected from amino acid sequences of SEQ ID NO: 2, SEQ ID NO: 4, or SEQ ID NO: 6.

(11) The antibody of (10), wherein the antibody is a monoclonal antibody.

(12) An immunoassay method for measuring the protein of (2) or its fragment, the method comprising immunologically binding the antibody of any one of (10) and (11), to the protein of (2) or its fragment.

(13) A reagent for an immunoassay for the protein of (2) or its fragment, comprising the antibody of any one of (10) and (11).

(14) A method for detecting mesangial proliferative nephropathy, the method comprising measuring the protein of (2) or its fragment contained in biological samples and comparing the measured amount with that obtained from normal samples.

(15) A transgenic nonhuman vertebrate, wherein the expression level of the gene encoding MEGSIN is modified.

(16) The transgenic nonhuman vertebrate of (15), wherein the nonhuman vertebrate is a mouse.

(17) The transgenic nonhuman vertebrate of (16), which is a knockout mouse wherein expression of the gene encoding MEGSIN is inhibited.

A full length cDNA library often comprises the sequences with different 5' ends in the same transcript due to the partial degradation of mRNA and the incomplete synthesis of the first strand. In addition, the nucleotide sequence of the 3' end is difficult to determine by the chain termination method using general primers due to the gap of primer extension on poly (A). A random prime cDNA library used for constructing EST data base is useful for finding a novel gene, however, can not be used for obtaining typical sequences of genes because it is not clear whether two partial sequences form different parts of a gene, or different transcripts. Therefore the present inventors used 3'-directed cDNA library. Through this method, unstable cloning efficiency reflecting the size of cDNA can be avoided. The sequence at the 3' region is typical, and the sequence data of about 200 to 300 bp are large enough for investigating the characteristics of a gene.

The DNA encoding human MEGSIN of the present invention can be obtained by preparing mRNA from mesangial cells and converting them to the double stranded cDNA by the known methods. mRNA can be prepared by, for example, the guanidine isothiocyanate-cesium chloride method (Chirwin, et al., Biochemistry 18, 5294, 1979), and the treatment with a surfactant and phenol in the presence of deoxyribonuclease (Berger & Birkenmeier, Biochemistry 18, 5143, 1979), etc. Poly $(A)^+$ RNA can be prepared from total RNA by, for example, the affinity chromatography using such a carrier bound to oligo (dT) as Sepharose, cellulose, latex particles, etc. DNA (cDNA) complementary to the mRNA can be obtained by treating RNA obtained in the above manner as a template with reverse transcriptase using oligo (dT) complementary to poly (A) strand at 3' end a random primer, or a synthetic oligonucleotide corresponding to a part of amino acid sequence of MEGSIN as primers. Hybrid mRNA-cDNA strand thus obtained can be converted to a double stranded cDNA by replacing the mRNA with a DNA strand by, for example, treating with *E. coli* RNase H, *E. coli* DNA polymerase I, and *E. coli* DNA ligase.

The DNA can be cloned by RT-PCR method using poly $(A)^+$ RNA from mesangial cells as a template, primers synthesized based on the human MEGSIN gene nucleotide sequence. Alternatively, without using PCR, the target cDNA can be obtained by directly screening a cDNA library with a probe synthesized based on human MEGSIN gene nucleotide sequence. The gene of the present invention can be selected by confirming the nucleotide sequence of the gene among the genes obtained by these methods. For mouse and rat MEGSIN, cDNA can be obtained by the same method.

Mouse and rat MEGSIN cDNA can be isolated as follows. mRNA is extracted from tissues of a mouse or rat, or cultured mesangial cells using three kinds of probes based on from the above human MEGSIN cDNA, which are a relatively highly conserved region (197-380 A. A.), a relatively less conserved region (1-196 A. A.), compared with genes of other SERPIN super family protein, and full length cDNA of MEGSIN open reading frame (1-380 A. A.) to construct a cDNA library. Colony hybridization is then performed using the above library or a commercially available cDNA library (Funakoshi). Alternatively, as similar to the probe preparation above, primers can be designed based on a relatively highly conserved region (197-380 A. A.) and a relatively less conserved region (1-196 A. A.), and RT-PCR can be conducted using mRNA extracted from tissues of a mouse or rat, or cultured mesangial cells for cloning to obtain mouse or rat MEGSIN cDNA. The genome can be obtained by conducting plaque hybridization method using a commercially available library (Funakoshi) in the same manner as in the case of obtaining the human genome.

Human MEGSIN genome can be obtained by plaque hybridization method (refer to Shin Saibou Kougaku Jikken (New Cell Biotechnology Experiment) Protocols, Shujunsha, pp 79-92) using the whole region of known MEGSIN cDNA open reading frame (1143 bp) or using as a probe each exon-intron part obtained by amplifying human genomic DNA through PCR method using a part of cDNA as primers as a probe, and a genomic library obtained by inserting DNA partially digested genomic DNA prepared from human B lymphoblast with Sau3 into phage vector EMBL3, or by inserting a human X chromosome library into phage vector Charon 35 (refer to Blood, vol. 83, No. 11, 1994, pp 3126-3131). A sequence of 5' UT region of the control region sequence can be determined by 5' RACE method (5'-Full RACE Core Set, following Takara's protocol) using human cultured mesangial cell-derived mRNA or human renal mRNA (purchased from Clontech) as a template.

The gene of the present invention can also be produced by following the standard methods using chemical synthesis of nucleic acids, such as phosphoamidite method (Mattencci, M. D. & Caruthers, M. H. J. Am. Chem. Soc. 103, 3185, 1981), phosphite triester method (Hunkapiller, M. et al., Nature 310, 105, 1984).

An eukaryotic gene often shows polymorphism, like human interferon gene, and one or more amino acids may be replaced by this polymorphism with maintaining activities of a protein. In general, activities of proteins can be often maintained even if one or more amino acids are modified. Therefore, any gene encoding a protein obtained by using the artificially modified gene encoding an amino acid sequence of SEQ ID NO: 2, SEQ ID NO: 4, or SEQ ID NO: 6 is included in this invention as long as the protein possesses the function typical to the gene of the present invention. The present invention includes any protein in which an amino acid sequence of SEQ ID NO: 2, SEQ ID NO: 4, or SEQ ID NO: 6 is artificially modified as long as it has characteristics of the proteins of the present invention.

The proteins of the present invention comprise an amino acid sequence of SEQ ID NO: 2, SEQ ID NO: 4, or SEQ ID NO: 6, or the amino acid sequences in which one or more amino acids are replaced, deleted, added, and/or inserted, and belong to the SERPIN super family. The SERPIN super family means proteins whose amino acid sequence is at least 20% identical to primary serine protease inhibitors in blood, such as antithrombin III, heparin cofactor II, α1-antitrypsin, α1-antichymotrypsin, protein C inhibitor, α2-plasmin inhibitor, C1 inhibitor, etc., and which does not necessarily show serine protease inhibitory activity (refer to R. Carrell et al., Trends Biochem. Sci. 10, 20, 1985; R. Carrell et al., Cold Spring Harbor Symp. Quant. Biol. 52, 527, 1987; E. K. O. Kruithof et al., Blood 86, 4007, 1995, J. Potempa et al., J. Biol. Chem. 269, 15957, 1994; and E. Remold-O'Donnell. FEBS Let. 315, 105, 1993).

The proteins of the present invention include a "protein comprising the amino acid sequence of SEQ ID NO: 2, SEQ ID NO: 4, or SEQ ID NO: 6, or the amino acid sequence in which one or more amino acids are replaced, deleted, or added, and/or inserted, and expressed weakly in human fibroblasts, smooth muscle cells, endothelial cells, keratinocytes, and expressed in mesangial cells." Alternatively, the proteins of the invention include a "protein comprising the amino acid sequence of SEQ ID NO: 2, SEQ ID NO: 4, or SEQ ID NO: 6, or the amino acid sequence in which one or more amino acids in these amino acid sequences are replaced, deleted, added, and/or inserted, and strongly expressed especially in mammalian mesangial cells." Moreover, the proteins of the present invention include a "protein comprising the amino acid sequence of SEQ ID NO: 2, SEQ ID NO: 4, or SEQ ID NO: 6, or the amino acid sequence in which one or more amino acids are replaced, deleted, added, and/or inserted, and comprising serine protease inhibitory activity," etc. These analogues are all encompassed by MEGSIN of the present invention. Therefore, not only human, rat, and mouse MEGSIN which structure is specifically described, but also the homologues of other species structurally or functionally equivalent to these are included in the current invention.

The DNA of the present invention includes DNAs encoding these proteins. The DNAs encoding these proteins can be cDNA, genomic DNA, or synthetic DNA.

The codons for desired amino acids themselves are well-known, can be optionally selected, and can be determined by following the standard method by, for example, considering the frequency of use of codons in hosts to be used (Grantham, R. et al. Nucleic Acids Res. 9, r43, 1981). Therefore, the present invention includes DNAs modified by degeneration of codons. These partial modifications of codons of nucleic acid sequence can be performed by site specific mutagenesis using primers composed of synthetic oligonucleotide encoding desired modification following standard methods (Mark, D. F. et al. Proc. Natl. Acad. Sci. U.S.A. 81, 5662, 1984).

Any DNA hybridizing with DNA containing the nucleotide sequence of SEQ ID NO: 1, SEQ ID NO: 3, or SEQ ID NO: 5, and encoding a protein that typically functions as MEGSIN of the present invention, can be included in the DNA of the present invention. A sequence capable of hybridizing with the above sequences under the stringent condition is thought to have the activities similar to a protein encoded by the above sequences.

The nucleotide sequences of DNAs of the present invention, including mutants, can be used for various purposes based on known techniques.

Other prokaryotic or eukaryotic hosts can be transformed by inserting the gene encoding MEGSIN cloned as described above into an appropriate vector. Moreover, the gene can be expressed in each host cell by introducing an appropriate promoter and sequences relating to the phenotypic expression into the vector. As an expression vector, for example, pET-3 (Studier & Moffatt, J. Mol. Biol. 189, 113, 1986), etc. for *E. coli*, pEF-BOS (Nucleic Acids Research 18, 5322, 1990) and pSv2-gpt (Mulligan & Berg, Proc. Natl. Acad. Sci. U.S.A. 78, 2072, 1981), etc. for COS cells, and pVY1 (WO89/03874), etc. for CHO cells can be used. The target proteins can be expressed as a fusion protein derived from a fusion gene between a target gene and a gene encoding other polypeptide. Such fusion proteins can easily be purified and separated to isolate a desired protein.

*Escherichia coli* can be used as prokaryotic host cells in the expression system of the present invention. *Saccharomyces cerevisiae*, etc. can be used as host cells among eukaryotic organisms. Examples of mammalian host cells include COS cells, CHO cells, BHK cells, etc. The transformants of the current invention can be cultured under appropriately selected culturing condition suitable for host cells.

MEGSIN can be produced by culturing the transformants transformed with the gene encoding the target MEGSIN, and recovering it from the microbial cells or the culture supernatant. It can be purified into a substantially pure protein. MEGSIN, a target protein of the present invention, can be separated and purified by the separation and purification methods commonly used for proteins, and the method is not particularly limited. MEGSIN can be separated and purified by, for example, appropriately selecting and combining various chromatographies.

Besides the methods described above, the gene of the present invention, the recombinant vector comprising the gene, the transformants carrying the vector and the production of MEGSIN using gene manipulation can be manipulated by the standard method described in "Molecular Cloning—A Laboratory Manual" (Cold Spring Harbor Laboratory, N.Y.).

In addition, a probe for detecting a MEGSIN gene can be designed based on the nucleotide sequence of SEQ IN NO. 1, SEQ IN NO. 3, or SEQ IN NO. 5. Moreover, primers for amplifying DNA and RNA containing these nucleotide sequences can be designed. It is routine for a person skilled in the art to design probes and primers based on a given sequence. An oligonucleotide comprising a designed nucleotide sequence can be chemically synthesized. These oligonucleotides can be used for the hybridization assay of various formats, or for the synthetic reaction of nucleic acids, such as PCR, if appropriately labeled. An oligonucleotide used as a probe or a primer has at least 15 bases, and preferably 25 to 50 bases.

A promoter region and an enhancer region of MEGSIN gene existing in genome can be obtained based on the cDNA nucleotide sequence of MEGSIN of the present invention. Specifically, these control regions can be obtained by the same method as described in unexamined published Japanese patent application (JP-A) No. Hei 6-181767, The Journal of Immunology, 1995, 155, 2477-2486, Proc. Natl. Acad. Sci. USA, 1995, 92, 3561-3565 etc. Herein, a promoter region means DNA region existing upstream of a transcription initiation site to control the expression of a gene, and an enhancer region means DNA region existing in an intron or 3' noncoding region to control expression of a gene.

Specifically, a promoter region can be obtained, for example, by the following method.
1) A promoter region of MEGSIN is cloned from a human genomic library using 5' end site of cDNA of MEGSIN as a probe.
2) MEGSIN gene is digested with restriction enzyme to obtain a DNA comprising the promoter region at the upstream region (2 to 5 kbp) containing a translation initiation codon of MEGSIN gene and determine the nucleotide sequence. The transcription initiation site (+1) is determined using poly (A)-RNA prepared from human mesangial cells as a template, by the primer elongation method using primer DNA selected from cDNA sequence at 5' end site of MEGSIN gene. A site possibly comprising the promoter activity is predicted by searching transcription factor binding sequence from the nucleotide sequence.
3) The DNA fragment excluding the coding region of MEGSIN gene from the DNA obtained in 2) is subcloned in a plasmid, and a chloramphenicol acetyl transferase (CAT) gene or a luciferase gene is ligated as a reporter gene at 2 to 5 kbp downstream of the DNA fragment to construct a reporter plasmid. Similarly, DNA fragments corresponding to various sites upstream of MEGSIN gene, in which 5' and 3' end sites are stepwise removed, are prepared by digestion with restriction enzymes or by PCR to include possible promoter regions. The CAT gene or the luciferase gene is ligated as a reporter gene at downstream of these DNA fragments to construct a reporter plasmid.

4) A promoter region upstream of MEGSIN gene is obtained by measuring CAT or luciferase activity in animal cells transformed with the reporter plasmid prepared in 3).

A 3' noncoding region and an enhancer region having an enhancer activity in introns can be obtained by cloning genomic genes of human MEGSIN from a human genomic library using MEGSIN cDNA as a probe in the same manner as described above for the promoter.

Transcription factors controlling the expression of MESGSIN gene can be obtained by the known methods, for example, those described in "Shin Saibou Kougaku Jikken (New Cell Biology Experiment) Protocols, Shujun-sha," "Biomanual series 5 Tensha Inshi Kenkyu-hou (studies on transcription factors), Yodo-sha," "DNA & Cell Biology, 13, 731-742, 1994," such as affinity chromatography, Southwestern method, footprinting method, gel shift method, or one-hybrid method. Herein, a transcription factor means a factor controlling the transcription of MEGSIN gene, including a transcription initiation factor that induces the transcription initiation reaction and a transcription control factor that up- or downregulates transcription. Affinity chromatography can be performed by applying a nucleic extract to an affinity column in which promoter and enhancer regions obtained above are immobilized on Sepharose or latex beads, washing the column, eluting the binding transcription factor using a DNA comprising the same sequence as that immobilized in the column, and recovering the transcription factor controlling the expression of MEGSIN gene.

In the case of South-western method, cDNA is inserted into an *E. coli* expression vector such as λgt11, to synthesize a fusion protein with β-galactosidase. The fusion protein is adsorbed on a nitrocellulose membrane, and a phage which synthesizes the fusion protein showing binding activities is selected using radiolabeled DNA fragments of promoter and enhancer regions as probes to obtain the transcription factor controlling the expression of MEGSIN gene.

The present invention also provides an antibody recognizing MEGSIN. The antibody of the present invention includes, for example, an antibody to the protein comprising the amino acid sequence of SEQ ID NO: 2, SEQ ID NO: 4, or SEQ ID NO: 6. An antibody (for example, a polyclonal antibody, a monoclonal antibody) or an antiserum against MEGSIN or a partial peptide of MEGSIN of the present invention can be produced by a known method for producing an antibody and antiserum, using MEGSIN of the present invention, a partial peptide of MEGSIN of the present invention, or a fusion protein such as His-Tag-MEGSIN or MBP-MEGSIN of the present invention as a antigen. A monoclonal antibody can be produced by, for example, the following method.

The MEGSIN of the present invention or a partial peptide of MEGSIN of the present invention is administered alone or together with a carrier or diluent to a warm-blooded animal at the site capable of producing an antibody. To enhance the antibody productivity, the complete Freund's adjuvant or incomplete Freund's adjuvant can be administered together with the antigen. Immunization is performed every one to six weeks, a total of about 2 to 10 times, in general. Warm-blooded animals to be used are, for example, a monkey, rabbit, dog, guinea pig, mouse, rat, sheep, goat, and domestic fowl, and preferably a mouse and rat. Monoclonal antibody-producing cells can be prepared by selecting immunized warm-blooded animals, such as mice, in which an antibody titer is detected, obtaining spleen or lymph node from the animals 2 to 5 days after the final immunization, and fusing the antibody producing cells contained in these tissues with myeloma cells to obtain monoclonal antibody-producing hybridoma. The antibody titer in antiserum can be measured by reacting the labeled MEGSIN described below with antiserum, and measuring an activity of the label binding to the antibody. Cell fusion can be performed by a known method, for example, the method of Kohler and Milstein (Nature, 256, 495, 1975). Polyethylene glycol (PEG), Sendai virus, etc. can be used as a fusion enhancer, and PEG is preferable.

Examples of myeloma cells include X-63Ag8, NS-1, P3U1, SP2/0, AP-1, etc., and X-63Ag8 is preferably used. The ratio of the number of antibody-producing cells (splenic cells) to that of myeloma cells is 1:20 to 20:1. Cells can be fused efficiently by adding PEG (preferably PEG1000 to PEG6000) at the concentration of about 10 to 80%, and incubating for 1 to 10 min at 20 to 40° C., preferably at 30 to 37° C. Anti-MEGSIN antibody-producing hybridoma can be screened by various methods, for example, the method in which the hybridoma culture supernatant is added to a solid phase (for example, a microplate) on which MEGSIN antigen is adsorbed directly or with a carrier, and anti-immunoglobulin antibody labeled with a radioactive substance or an enzyme (When cells used for cell fusion are derived from a mouse, anti-mouse immunoglobulin antibody is used.) or protein A is added thereto, and anti-MEGSIN monoclonal antibody binding to the solid phase is detected, the method in which the hybridoma culture supernatant is added to a solid phase on which anti-immunoglobulin antibody or protein A is adsorbed, and MEGSIN labeled with a radioactive substance or an enzyme is added thereto, and anti-MEGSIN monoclonal antibody binding to the solid phase is detected.

Anti-MEGSIN monoclonal antibody can be selected and cloned by known methods or modified methods thereof using usually a culture medium for animal cells supplemented with HAT (hypoxanthine, aminopterin, and thymidine). Any medium for selection, cloning, and culturing can be used as long as hybridoma can grow therein,. For example, RPMI 1640 medium (Dainippon Pharmaceutical Co., Ltd.) containing 1 to 20%, preferably 10 to 20% of fetal bovine serum, GIT medium (Wako Pure Chemicals) containing 1 to 10% fetal bovine serum, or serum-free medium for hybridoma culturing (SFM-101, Nissui Pharmaceutical Co., Ltd.) can be used. Incubation temperature is generally 20 to 40° C., preferably about 37° C. Incubation time is generally 5 days to 3 weeks and preferably 1 to 2 weeks. Incubation is performed under the 5% carbon dioxide gas in general. The antibody titer of the hybridoma culture supernatant can be determined in the same manner as described above for the measurement of anti-MEGSIN antibody titer in the antiserum. Cloning can be generally conducted by known methods, for example, semisolid agar method, or limiting dilution method. A cloned hybridoma is cultured preferably in a serum-free medium, thereby producing an optimal amount of an antibody in the supernatant. Preferably, a target monoclonal antibody can be obtained in ascites.

A monoclonal antibody of the present invention does not crossreact with other proteins other than MEGSIN by selecting those capable of recognizing epitopes specific to MEGSIN. In general, an epitope specific to a protein is composed of at least 7 or more continuous amino acid residues, preferably 10 to 20 amino acids in an amino acid sequence of the protein. Therefore, a monoclonal antibody recognizing an epitope composed of peptides having an amino acid sequence selected from the amino acid sequence of SEQ ID NO: 2, SEQ ID NO: 4, or SEQ ID NO: 6, and composed of at least 7 continuous amino acid residues can be the monoclonal antibody specific to MEGSIN of the present invention. Conserved amino acid sequences among the amino acid sequences of SEQ ID NO: 2, SEQ ID NO: 4, and SEQ ID NO: 6 can be selected to choose epitopes common in the MEGSIN family. If a region contains amino acid sequences specific to all sequences, a monoclonal antibody capable of recognizing different species can be selected.

An anti-MEGSIN monoclonal antibody can be separated and purified by the separation and purification method of immunoglobulin commonly used for the separation and purification of polyclonal antibodies. The known purification methods include, for example, salting out, alcohol precipitation, isoelectric point precipitation, electrophoresis, adsorption and desorption method by ion exchanger (for example, DEAE), ultra centrifugation, gel filtration, or specific purification method whereby antibody is exclusively collected by, for example, an antigen binding solid phase or active adsorbent, such as Protein A or Protein G, and the binding is dissociated to obtain the antibody.

Monoclonal antibodies and polyclonal antibodies recognizing MEGSIN of the present invention, obtained in such a manner, can be used for the diagnosis and treatment for diseases relating to mesangial cells. Examples of a method for measuring MEGSIN with these antibodies include an sandwich assay comprising reacting MEGSIN with an antibody binding to an insoluble carrier and a labeled antibody and detecting MEGSIN in the sandwiched complex produced by the reaction, or a competition method comprising competitively reacting labeled human urine-derived MEGSIN and human urine-derived MEGSIN in a sample with an antibody to measure human urine-derived MEGSIN in a samples based on labeled antigen amount reacted with the antibody.

The measurement of human urine-derived MEGSIN by the sandwich method is conducted by the 2 step method in which an immobilized antibody is reacted with human urine-derived MEGSIN, unreacted materials are completely removed by washing, and a labeled antibody is added to form a complex of the immobilized antibody, the labeled human urine-derived MEGSIN antibody, or one step method in which the immobilized antibody, the labeled antibody, and human urine-derived MEGSIN are mixed at the same time.

Examples of an insoluble carrier used for the measurement include, for example, polystyrene, polyethylene, polypropylene, polyvinyl chloride, polyester, polyacrylate, nylon, polyacetal, synthetic resin such as fluoride resin, etc., polysaccharides such as cellulose, agarose, etc., glass, metals, etc. The form of an insoluble carrier can be varied and includes tray, spheroid, fiber, stick, board, container, cell, test tube, etc. The antibody-adsorbed carrier should be stored at a cool place in the presence of appropriate preservatives, such as sodium azide.

Antibodies can be immobilized by known chemical binding or physical adsorption methods. Chemical binding methods include, for example, a method using glutaraldehyde, the maleimide method using N-succinimidyl-4-(N-maleimidomethyl)cyclohexane-1-carboxylate, N-succinimidyl-2-maleimidoacetate, etc., and the carbodiimide method using 1-ethyl-3-(3-dimethylaminopropyl)carbodiimide hydrochloride, etc. In addition, the maleimidobenzoyl-N-hydroxysuccinimidoester method, the N-succimidyl-3-(2-pyridyldithio)propionate method, the bisdiazolated benzidine method, and dipalmityllysine method. Alternatively, the complex produced by reacting two different antibodies against a substance to be detected and an epitope is captured with the third antibody immobilized by the above method.

Any label useful for immunoassay can be used without being limited. Specifically, enzymes, fluorescent substances, luminescent substances, radioactive substances, metal chelates, etc. can be used. Preferable labeling enzymes are, for example, peroxidase, alkaline phosphatase, β-D-galactosidase, malate dehydrogenase, *Staphylococcus* nuclease, delta-5-steroid isomerase, α-glycerol phosphate dehydrogenase, triosephosphate isomerase, horseradish peroxidase, asparaginase, glucose oxidase, ribonuclease, urease, catalase, glucose-6-phosphate dehydrogenase, glucoamylase, and acetylcholine esterase, etc. Preferable fluorescent substances include, for example, fluorescein isothiocyanate, phycobiliprotein, rhodamine, phycoerythrin, phycocyanin, allophycocyanin, and orthophthalaldehyde. Preferable luminescent substances include, for example, isoluminol, lucigenin, luminol, aromatic acridiniumester, imidazole, acridinium salt and its modified ester, luciferin, luciferase, and aequorine. Preferable radioactive substances include, for example, $^{125}I$, $^{127}I$, $^{131}I$, $^{14}C$, $^{3}H$, $^{32}P$, $^{35}S$, etc.

The method for binding the above labels is known. Specifically, direct and indirect labeling can be used. The common direct labeling is the method in which an antibody or an antibody fragment is chemically covalent-bound with a label using a crosslinking agent. Crosslinking agents include N,N'-orthophenylenedimaleimide, 4-(N-maleimidomethyl) cyclohexanoate N-succinimide ester, 6-maleimidohexanoate N-succinimide ester, 4,4'-dithiopyridine, and other known crosslinking agents. The crosslinking agent can be reacted with enzymes and antibodies by the known methods depending on the characteristics of the crosslinking agent. An example of the indirect labeling method comprises binding an antibody to a low molecular weight hapten such as biotin, dinitrophenyl, pyridoxal, or fluorescamine, and indirectly labeling the antibody with the binding partner to the hapten. Avidin and streptoavidin can be used as a recognition ligand for biotin, whereas dinitrophenyl, pyridoxal, or fluorescamine are labeled with antibodies recognizing these haptens. Horseradish peroxidase can be used as a enzyme for labeling antibodies. This enzyme is useful because it can react with many substrates and be easily bound to antibodies by the periodate method. Occasionally, as an antibody, their fragments, for example, Fab', Fab, F(ab')$_2$ are used. Both polyclonal and monoclonal antibodies can be labeled with an enzyme by the same method. Enzyme-labeled antibodies obtained using the above crosslinking agent can be purified by the known methods such as affinity chromatography, etc. to serve in a more sensitive immunoassay system. Purified enzyme-labeled antibodies are stored with a preservative such as thimerosal and a stabilizer such as glycerol. Labeled antibodies can be lyophilized and stored in the cool and dark place for a long time.

When a label is an enzyme, its substrate and, if necessary, a coloring agent are used for measuring its activity. When peroxidase is used as an enzyme, $H_2O_2$ is used as a substrate solution and 2,2'-azino-di-[3-ethylbenzothiazolinesulfonic acid] ammonium salt (ABTS), 5-aminosalicylic acid, orthophenylenediamine, 4-aminoantipyrine, or 3,3',5,5'-tetramethylbenzidine, etc. is used as a coloring agent. When alkaline phosphatase is used as an enzyme, orthonitrophenylphosphate, paranitrophenylphosphate, etc. can be used as substrates. When β-D-galactosidase is used as an enzyme, fluorescein-di-(β-D-galactopyranoside), 4-methylumbelliferyl-β-D-galactopyranoside, etc. can be used as substrates. The present invention also includes an immunoassay reagent for MEGSIN, comprising labeled or immobilized monoclonal or polyclonal antibodies, and further includes a kit comprising this reagent and an indicator for detection label and a control sample, etc.

Any biological samples such as body fluid such as blood plasma, serum, blood, urine, tissue fluid, or cerebrospinal fluid etc. can be used as samples for measuring the MEGSIN of the present invention as long as they contain MEGSIN or its precursor or a fragment. Among these biological samples, especially in urine, MEGSIN can be detected with high frequency, accompanied by proliferation and activation of mesangial cells. Measurement of MEGSIN in urine is useful as a marker for mesangial proliferative nephropathy, such as IgA nephropathy.

In addition, the present invention relates to a transgenic nonhuman vertebrate animal in which the expression level of MEGSIN gene is altered. Herein, MEGSIN gene includes cDNA, genomic DNA, or synthetic DNA encoding MEGSIN. Gene expression includes both steps of transcription and translation. Transgenic animals of the present invention are useful for investigating function and expression control of MEGSIN, clarifying mechanisms of development of diseases relating to human mesangial cells, and developing disease model animals used for screening and testing safety of pharmaceuticals.

In the present invention, MEGSIN gene can be modified so as to artificially increase or decrease its expression level compared with the original gene by introducing mutation such as deletion, substitution, insertion, etc. in a part of some important sites (enhancer, promoter, intron, etc.) which control the normal expression of MEGSIN gene. Such modification alters transcription of MEGSIN gene. On the other hand, translation to proteins can be modified by deleting a part of an exon, or replacing a certain codon with a stop codon by introducing point mutation into coding regions. Such mutation can be introduced by the known methods for obtaining transgenic animals.

Transgenic animals means, in a narrow sense, animals into reproductive cells of which an exogenous gene is artificially introduced by genetic recombination, and in a broad sense, animals into chromosome of which an exogenous gene is stably introduced during an early developmental stage, said gene can be transmitted to the offspring as genotype, including antisense transgenic animals in which the function of a specific gene is inhibited by antisense RNA, animals in which a specific gene is knocked out by using embryonic stem cells (ES cells), and animals into which point mutation DNA is introduced. Transgenic animals used herein include all vertebrates except for human.

Transgenic animals can be prepared by the method comprising mixing a gene with an egg and treating the mixture with calcium phosphate, the microinjection method whereby a gene is directly injected into a nucleus in pronuclear egg by a micropipette under the phase contrast microscope (microinjection method, U.S. Pat. No. 4,873,191), and the method using embryo stem cells (ES cells). Other methods include, for example, the method in which a gene is inserted into a retrovirus vector to infect an egg and the sperm vector method in which a gene is introduced into an egg through sperm, etc. The sperm vector method is a genetic recombination method for introducing an exogenous gene by attaching an exogenous gene into sperm or incorporating an exogenous gene into sperm cells by electroporation, etc. and fertilizing an egg (M. Lavitranoet et al., Cell, 57, 717, 1989).

In vivo Site specific genetic recombination such as cre/1oxP recombinase system of bacteriophage P1, FLP recombinase system of *Saccharomyces cerevisiae*, etc. can be used. The method for introducing a transgene of a target protein into nonhuman animals using retrovirus has been reported.

Transgenic animals can be prepared by microinjection, for example, in the following manner. A transgene basically composed of a promoter regulating expression, a gene encoding a specific protein, and polyA signal is provided. Expression pattern and level for all lineages should be confirmed since the expression pattern and level of a specific molecule depend on the promoter activity, and prepared transgenic animals vary among lineages depending on the number of copies and introduction site on chromosomes of an introduced transgene. A sequence of introns to be spliced at upstream of polyA signal may be introduced when the expression level is known to vary depending on noncoding region and splicing. It is important to use a gene as pure as possible for introducing into a fertilized egg. An animal to be used includes a mouse for collecting fertilized eggs (5 to 6 weeks old), male mouse for crossing, pseudopregnant female mouse, vasoligated male mouse, etc.

To efficiently obtain fertilized eggs, ovulation can be induced by gonadotropin, etc. A fertilized egg is collected, and a gene is injected into a male pronucleus of the egg by microinjection using an injection pipette. Animals for returning the treated eggs into an oviduct are prepared (pseudopregnant female mice, etc.), and about 10 to 15 eggs are transplanted per each individual. Introduction of the transgene into a new-born mouse is confirmed by extracting genomic DNA from the tip of the tail and detecting the transgene by Southern hybridization or PCR methods, or by the positive cloning method in which a marker gene that is activated only upon homologous recombination is inserted. Expression of the transgene can be confirmed by detecting a transgene-derived transcript by Northern hybridization or RT-PCR methods. Detection by Western blotting method is also possible using a antibody specific to a protein.

A knockout mouse of the present invention is prepared so as to lose the function of MEGSIN gene. A knockout mouse means a transgenic mouse in which a certain gene is destroyed by homologous recombination technology to eliminate its function. A knockout mouse can be prepared by conducting homologous recombination using ES cells and selecting ES cells in which one allele is modified and destroyed. For example, genetically manipulated ES cells are injected into a blastocyst or an 8-cell embryo of an fertilized egg to obtain a chimeric mouse having both cells derived from ES cells and from embryo. A heterozygous mouse in which all of one allele is modified and destroyed can be prepared by crossing a chimeric mouse (chimera means an individual composed of somatic cells derived from two or more fertilized eggs) and a normal mouse. Crossing of heterozygous mice with each other can produce homozygous mice. A transgenic animal of the present invention includes both heterozygotes and homozygotes.

Homologous recombination means the recombination occurring between two genes whose nucleotide sequences are the same or extremely similar through mechanism of genetic recombination. Cells with homologous recombination can be selected by PCR. Homologous recombination can be confirmed by performing PCR using as primers sequences of a part of a gene to be inserted and a part of a chromosomal region into which the gene is expectedly inserted and detecting cells producing amplified products. Homologous recombination in the genes expressed in ES cells can be easily screened by known methods or their modified methods, for example, by binding neomycin resistant gene to the introduced gene to make the cells neomycin resistant after the introduction.

BRIEF DESCRIPTION OF THE DRAWINGS

FIG. 1 shows the amino acid sequence of MEGSIN. The underlined part shows "SERPIN" signature. The boxed part and the arrow show reactive site loop (RSL) and putative reaction site, respectively. The two putative hydrophobic regions are indicated by the dotted lines.

BEST MODE FOR IMPLEMENTING THE INVENTION

Figures 2A, 2B:
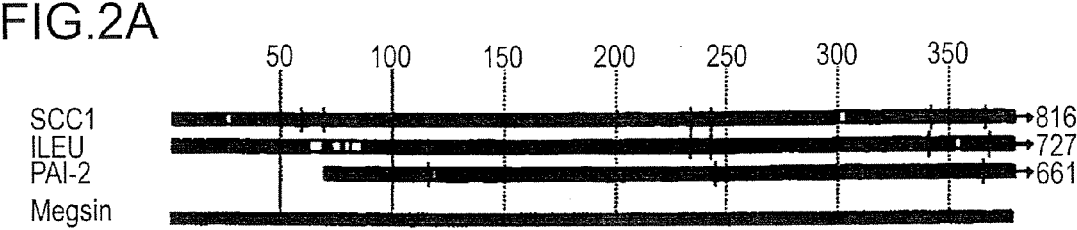
FIG. 2 shows the comparison of amino acid sequences of MEGSIN with other proteins belonging to SERPIN super family. In panel (A), homologous regions are indicated by the bars. Gaps between the bars show spaces inserted in database sequences for the optimization of alignment, and the lines across the bars show the regions where residues are inserted into database sequences compared with the subject sequence. These sequences are aligned by following the protein scoring matrix pam 250. The scores are shown at the right of the bars (a maximum potential score is 1820). Panel (B) shows the comparison of RSL of SERPIN. P17-P5' of RSL is aligned (based on numbering by Schecher and Berger). Nonpolar residues are shown by the bold letters. "SCC1," "ILEU," "PAI-2," and "ova" represent squamous epithelial cell carcinoma antigen 1 (SCCA1), elastase inhibitor, plasminogen activator inhibitor-2 (PAI-2), and ovalbumin respectively.

The present invention is illustrated in detail below with references to examples, but is not to be construed as being limited thereto.

EXAMPLE 1

Primary Culture of Human Mesangial Cells

Human glomerular renal mesangial cells were isolated from the normal human kidney excised from a 58 year-old male. Renal cortex was separated under the sterilized condition, minced, and passed through several sieves. Pore diameters of the used sieves were decreased stepwise, and the trapped glomerulus by the sieve at the pore diameter of 75 to 200 mm was washed and incubated with 100 μg/ml collagenase (Washington Biochemical) at 37° C. for 20 min. After washing, the glomerulus was resuspended in medium 199 (Gibco BRL, Gaithersburg, Md.) containing 25 mM Hepes, 10% Nu-serum (Collaborative Biomedical Products, Bedford, Mass.), and antibiotics (100 mg/ml of penicillin, streptomycin, and Fungizone), and incubated in the 5% $CO_2$ incubator. At the third passage, mesangial cells were identified based on a series of criteria such as typical morphological characteristics, resistance to trypsin, puromycin, and D-valine, positiveness against immunostaining of actin (Zymed Laboratories, San Francisco, Calif.), anti-very late antigen (VLA)-1, 3, 5 (Immunotech), and negativeness against immunostaining of VIII factor (Dako, Calif.).

EXAMPLE 2

Isolation of mRNA from Human Cultured Mesangial Cells

At the sixth passage, total RNA was isolated from human mesangial cells using guanidine isothiocyanate (GTC) method. The confluent culture of the mesangial cells in the medium containing serum of the cells of Example 1 was washed with phosphate buffer saline (PBS), and dissolved in 5.5 mM GTC solution. DNA was removed by passing through an 18-gauge needle. Nuclei and other cell debris were precipitated by centrifugation at 5,000×g for 90 sec. Supernatant was carefully loaded on the layer of cesium trifluoroacetate (CSTFA) and centrifuged at 125,000×g at 15° C. for 24 hours. RNA pellet was dissolved in TE buffer. Poly (A)$^+$ RNA was isolated using oligo dT cellulose column (Pharmacia).

EXAMPLE 3

Construction of 3'-Directed cDNA Library cDNA was synthesized using the vector primer based on pUC19 (Norrander J. et al., Gene, 26, 101-106, 1983) with poly (A)$^+$ RNA as a template. This vector primer DNA comprised the HincII end and the PstI end with a T tale, and dam-methylated at the MboI site (GATC). After synthesizing the second strand, the cDNA sequence and the single BamHI site in LacZ gene of the vector were digested with MboI and BamHI, respectively, and circularizion and ligation were conducted at the low DNA concentration. A portion of the ligation mixture was transformed to E. coli. The obtained transformants were randomly selected and individually dissolved by simply heating. The inserted sequence of cDNA was amplified by the paired PCR using primers (5'-TGTAAAACGACGGCCAGT-3'/SEQ ID NO: 7 and 5'-ACCATGATTACGCCAAGCTTG-3'/SEQ ID NO: 8) flanking the pUC19 cloning site. The obtained short double stranded DNA was used for the cycle sequence determination reaction and analyzed by an automatic sequencer.

EXAMPLE 4

Isolation of Genes Expressed Specifically in Mesangial Cells

In order to identify genes expressed specifically in mesangial cells, the present inventors conducted large scale DNA sequencing and data processing by computers. Transcripts in the various different cells and organs could be simultaneously compared (Y. Yasuda et al., submitted; K. Matsubara et al., Gene. 35, 265, 1993; K. Okubo et al., Nat. Gen. 2, 173, 1992). Large scale DNA sequencing of the 3'-directed cDNA library of human cultured mesangial cells was conducted, and randomly selected 1836 clones were sequenced for their partial sequences. The sequence homology among clones was mutually compared, and further compared with that in DNA data bank GenBank using FASTA program. mRNA from various organs and cells were analyzed using dot blot to select clones expressed specifically in mesangial cells. Among clones detected exclusively in the mesangial cell cDNA library, the major clone was obtained. This clone contained 0.3% of total mRNA.

EXAMPLE 5

Cloning of Full Length Strand by 5' Race Method

The following experiment was carried out using "5'-Full RACE Core Set" (Takara). To a 0.5 ml microtube were added 4.0 µl of poly (A)$^+$ RNA (0.5 µg/µl) prepared from human cultured mesangial cells, 1.5 µl of 10×RT buffer, 0.5 µl of RNase inhibitor (40 U/µl), 1 µl of AMV Reverse Transcriptase XL (5 U/µl), 1 µl of 5' end phosphorylated RT primer (5'-pTCAGAGAGGTCATTC/SEQ ID NO: 9, 200 pmol/µl). The mixture was made up to 15 µl with 7 µl of RNase Free dH$_2$O. This reaction mixture was set in "Takara PCR Thermal Cycler" (Takara) and incubated at 30° C. for 10 min, at 50° C. for 60 min, 80° C. for 2 min, and at 40° C. for 10 min to obtain the first strand cDNA.

A 15 µl aliquot of the reaction mixture was added to a 0.5-µl microtube containing 15 µl of 5× hybrid RNA denaturation buffer and 45 µl of H$_2$O. RNaseH (1 µl) was added thereto, and reacted at 30° C. for 1 hour. After the completion of the reaction, 150 µl of ethanol was added thereto, cooled at −70° C. for 30 min, and centrifuged to remove supernatant and collect precipitate.

To the obtained precipitate were added 8 µl of 5×RNA (ssDNA) ligation buffer, 20 µl of 40% PEG #600, and 12 µl of H$_2$O. It was mixed well. T4 ligase (1 µl) was added thereto, and reacted at 16° C. for 15 hours to obtain the circularized single strand cDNA.

The obtained circularized single strand cDNA was diluted 10 fold with TE buffer and used as a template for the first PCR. The reaction mixture contained 5 µl of 10×LA PCR buffer II (Mg$^{2+}$ plus), 8 µl of dNTP mixture (2.5 mM), 0.5 µl of first PCR S1 primer (5'-TCATTGATGGGTCCTCAA/ SEQ ID NO: 10, 20 pmol/µl), 0.5 µl of first PCR A1 primer (5'-AGATTCTTGAGCTCAGAT/SEQ ID NO: 11, 20 pmol/ µl), and 0.5 µl of TaKaRa LA Taq™ (5 U/µl), which was made up to 50 µl with sterilized water. It was set in "Takara PCR Thermal Cycler" and reacted under the condition with 25 cycles of 94° C. for 30 sec, 60° C. for 30 sec, and 72° C. for 2 min after heated at 94° C. for 3 min.

The reaction mixture containing 1 µl of the first PCR product as a template, 5 µl of 10×LA PCR™ buffer II (Mg$^{2+}$ plus), 8 µl of dNTP mixture (2.5 mM), 0.5 µl of the second PCR S2 primer (5'-AATGGTGGCATAAACATG/SEQ ID NO: 12, 20 pmol/µl), 0.5 µl of the second PCR A2 primer (5'-ACAGACAAATTGAACTTC/SEQ ID NO: 13, 20 pmol/µl), and 0.5 µl of TaKaRa LA Taq TM (5 U/µl), which was made up to 50 µl with sterilized water, was set in "Takara PCR Thermal Cycler." The reaction was conducted under the condition with 30 cycles of 94° C. for 30 sec, 60° C. for 30 sec, and 72° C. for 2 min.

The obtained bands were confirmed by the 0.75% agarose gel electrophoresis and 1 µl from the product was subcloned using "Original TA Cloning Kit" (Invitrogen). The obtained plasmid was named as "pCR-942-5.3." The nucleotide sequence of the inserted gene fragment was sequenced by the dideoxy termination method.

The obtained nucleotide sequence contained about 600 nucleotides encoding the N-end of the gene product and about 400 nucleotides as the 5' noncoding region. The putative initiation codon ATG was coincident with the consensus sequence that provides the longest open reading frame (satisfying "the first ATG rule "). The nucleotide sequence of MEGSIN cDNA and the deduced amino acid sequence of MEGSIN were shown in SEQ ID NO: 1 and SEQ ID NO: 2, respectively.

EXAMPLE 6

Expression of Protein

In order to obtain a gene comprising coding regions, PCR reaction was conducted with 1.0 µl of poly (A)$^+$RNA (0.5 µg/µd) from human cultured mesangial cells as a template, and the primers designed so as to encode the coding regions, that is, the primer comprising the initiation codon with the restriction enzyme EcoRI recognition sequence at the 5' end (5'-GAATTCATGGCCTCCCTTGCTGCAGCAAA/SEQ ID NO: 14), and the primer with the stop codon and the SalI recognition sequence (5'-GTCGACTTATCAAGGGCAA-GAAACTTTGCC/SEQ ID NO: 15). The reaction mixture contained 5 µl of 10×Ex Taq buffer, 8 µl of dNTP mixture (2.5 mM), 0.5 µl of the PCR primer (5'-GTCGACTTAT-CAAGGGCAAGAAACTTTGCC/SEQ ID NO: 15, 20 pmol/µl), 0.5 µl of the first PCR A1 primer (5'-GAAT-TCATGGCCTCCCTTGCTGCAGCAAA/SEQ ID NO: 14, 20 pmol/µl), and 0.5 µl of TaKaRa Ex Taq TM (10U/µl), which was made up to 50 µl with sterilized water, and set in "Takara PCR Thermal Cycler" to react under the condition with 30 cycles of 94° C. for 1 mm, 60° C. for 2 mm, and 72° C. for 2 mm. The amplification was confirmed by 0.75% agarose gel electrophoresis, and 1 µl of the reactant was subcloned using "Original TA Cloning Kit" (Invitrogen). The obtained plasmid was named as pCR-942CD-11/2. *E.coli* JM 109 transformed with pCR-942CD-11/2 has been deposited at National Institute of Bioscience and Human-Technology, Agency of Industrial Science and Technology, Ministry of International Trade and Industry (Accession No. FERM BP-6518). This plasmid was digested with EcoRI and SalI. The inserted gene was ligated with EcoRI- and SalI-digested pMAL-c (New England Biolab), an expression vector for maltose binding protein-fusion protein, through T4 ligase, and *E. coli* XL1-Blue was transformed with this product. After 18 hours, the ampicillin resistant cells were added to 3 ml of LB medium and cultured for 18 hours. The plasmid was extracted by the miniprep method, and confirmed by the restriction enzymes to obtain expression vector pMAL-MEGSIN. *E. coli* XL1-Blue transformed with pMAL-MEGSIN has been internationally deposited at National Institute of Bioscience and Human-Technology, Agency of Industrial Science and Technology, Ministry of International Trade and Industry (Accession No. FERM BP-6517).

International deposit of *E. coli* JM 109 transformed with pCR-942CD-11/2:
(a) Address and Name of depositary institution
  Name: National Institute of Bioscience and Human-Technology, Agency of Industrial Science and Technology, Ministry of International Trade and Industry
  Address: 1-3, Higashi 1-Chome, Tsukuba-shi, Ibaraki-ken, Japan (zip code: 305-0046)
(b) Date of deposition (Original date of deposition) Sep. 22, 1997
(c) Accession No. FERM BP-6518

International deposit of *E. coli* XL1-Blue transformed with pMAL-MEGSIN:
(a) Address and name of depositary institution
  Name: National Institute of Bioscience and Human-Technology, Agency of Industrial Science and Technology, Ministry of International Trade and Industry
  Address: 1-3, Higashi 1-Chome, Tsukuba-shi, Ibaraki-ken, Japan (zip code: 305-0046)
(b) Date of deposition (Original date of deposit) Sep. 22, 1997
(c) Accession No. FERM BP-6517

*E. coli* XL-Blue transformed with pMAL-MEGSIN was added to 10 ml of LB medium containing 100 µg/ml ampicillin, and cultured at 37° C. for 18 hours with shaking. This cultured medium was added to 1 liter of Rich medium (containing 10 g of tryptone, 5 g of yeast extract, 5 g of NaCl, 2 g of glucose, and 100 µg/ml ampicillin) and cultured at 37° C. with shaking. When the culture medium reached about 0.4 OD (A600) measured by a turbidimeter, 3 ml of 0.1 M IPTG (1.41 g of isopropyl-β-D-thiogalactoside diluted with 50 ml of water) was added thereto, and further cultured at 37° C. with shaking. After 2 hours, the cells were collected by centrifugation (4000×g, 20 min), and 50 ml of lysis buffer (10 mM Na$_2$HPO$_4$, 30 mM NaCl, 0.25% Tween20, pH 7.0) was added. The cells were well suspended, frozen at −80° C. for 18 hours, and sonicated (SONIFIER 250: BRANSON) to destroy cells. NaCl was added thereto to 0.5 M and centrifuged (10000×g, 30 min) to collect supernatant, of 0.25% Tween 20/column buffer was added to the supernatant, and the mixture was loaded onto the column filled with 30 ml of amylose resin equilibrated with 0.25% Tween 20/column buffer (0.25% Tween 20, 10 mM phosphoric acid, 0.5 M NaCl, pH7.2). The column was washed with 100 ml of 0.25% Tween 20/column buffer at 1 ml/min flow rate, and then with 150 ml of column buffer. The fusion protein binding to the amylose resin was eluted with 50 ml of column buffer containing 10 mM maltose. This was concentrated to about 1 mg/ml by a ultrafiltration device (Amicon stirred-cell concentrator).

The fused maltose binding protein can be digested and removed by the enzymes through the following method. The protein solution is added to a dialysis tube (molecular weight cutoff: 3,500) and dialyzed against factor Xa buffer (20 mM Tris-Cl, 100 mM NaCl, 2 mM CaCl$_2$, and 1 mM sodium azide). Ten microliters of factor Xa (200 µl/ml) is added to 200 µl of the dialyzate (1 mg/ml), and the mixture is reacted for 24 hours at room temperature to specifically digest the biding site between the maltose binding protein and the target protein. After digestion, the target protein can be obtained by purification through gel filtration chromatography, ion exchange column chromatography, etc.

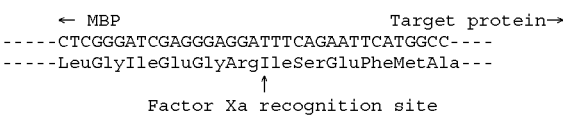

```
← MBP                       Target protein→
-----CTCGGGATCGAGGGAGGATTTCAGAATTCATGGCC----
-----LeuGlyIleGluGlyArgIleSerGluPheMetAla---
                          ↑
              Factor Xa recognition site
```

EXAMPLE 7

Function Analysis of Mesangial Specific Gene (1)

Amino acid homology search on SwissProt data base by FASTA program revealed that this gene product was highly homologous to the proteins belonging to SERPIN (serine protease inhibitor) super family (R. Carrell et al., Trends Biochem. Sci. 10, 20, 1985; R. Carrell et al., Cold Spring Harbor Symp. Quant. Biol. 52, 527, 1987; E. K. O. Kruithof et al., Blood 86, 4007, 1995; J. Potempa et al., J. Biol. Chem. 269, 15957, 1994; and E. Remold-O'Donnell., FEBS Let. 315, 105, 1993). SERPIN super family is a structurally relating protein group and generally functions as an extracellular irreversible serine protease inhibitor. Squamous epithelial cell carcinoma antigen 1 (SCCA1) showed the highest homology to the mesangial specific gene (41.2% identity), followed by the other proteins of SERPIN super family, SCCA2 (40.6%), leukocyte esterase inhibitor (37.5%), and plasminogen activator inhibitor 2 (PAI-2) (35.2%). The present inventors named this gene as MEGSIN (mesangial cell-specific gene with a homology to serpin).

The amino acid sequence of MEGSIN was subjected to motif-search (FIG. 1). First, it was found that the characteristic of SERPIN existed at the COOH end. Four putative N-glycosylated sites existed. Obvious NH$_2$ end signal peptide sequence was not detected, but two hydrophobic regions existed in αhelix A (amino acids 1 to 16) and αhelix B (amino acids 27 to 44). These are thought to play an important role in transfer of SERPIN (G. von Heijne et al., J. Biol. Chem. 266, 15240, 1991; D. Belin. Thromb. Haemost. 70, 144, 1993; and D. Belin et al. EMBO J. 15, 468, 1996). Some of SERPIN family proteins may be secreted by a non-degradable internal signal sequence in αhelix A and αhelix B, or exists as a dualistic molecule existing in cytoplasm (R. D. Ye et al., J. Biol. Chem. 263, 4869, 1988; A. Wohlwend et al., J. Immunol. 139, 1278, 1987; A. Wohlwend et al., J. Exp. Med. 165, 320, 1987; C. Genton et al., J. Cell Biol. 104, 705, 1987; and P. Mlkus et al., Eur. J. Biochem. 218, 1071, 1993). Comparison with other proteins of SERPIN super family indicated that amino acids 334 to 352 corresponded to the reactive site loop (RSL) (P16-p5') (P. C. Hopkins et al., Science 265, 1893, 1994; K. Aertgeerts et al., Nature Struct. Biol. 2, 891, 1995; P. A. Patston et al., FEBS Let. 383, 87, 1996; and H. T. Wright, BioEssays. 18, 453, 1996) (FIG. 2). Although some of SERPIN do not inhibit protease, transport hormones, or control blood pressure. There are three evidences showing that MEGSIN is a protease inhibitor. First, Peven residue of RSL in MEGSIN is not electrically charged, small, and nonpolar. These are characteristics of SERPIN protease inhibitors. Second, SERPIN protease inhibitors comprise the sequence of "Ala-Ala (Thr)-Ala-Ala"/SEQ ID NO: 45 at the $NH_2$ end region of RSL (P12-P9), called hinge region. P12-P9 of RSL in MEGSIN is "ATAA/336-339 (SEQ ID NO: 2)." The P17-P8 sequence of RSL in MEGSIN (EGTEATAAT/332-340 (SEQ ID NO: 2) is actually coincident with the consensus sequence (EGTEAAAAT/SEQ ID NO:46) of SERPIN protease inhibitors. Third, βsheet region exists just before the $NH_2$ end region of RSL. This is essential for protease inhibition and limits the size and electrical charge of amino acids in the hinge region for achieving appropriate change of conformation. MEGSIN conserves this βsheet region.

Residues flanking the bond which is deduced to be easily cleaved in RSL (P1 and P'1) are Lys-Gln, and are supposed to be important for determining substrate specificity (T. E. Creighton et al., J. Mol. Biol. 194, 11, 1987; P. Gettins et al., BioEssays. 15, 461, 1993; P. E. Stein et al., Struct. Biol. 2, 96, 1995). Any other SERPIN protease inhibitors having the sequence relating to this site are not known. SERPIN, such as Kunitz type bovine basic protease inhibitor, comprises Lys at P1 and strongly inhibits trypsin. The target serine protease of MEGSIN is, therefore, presumably lysine cleaving protease.

EXAMPLE 8

Function Analysis of MEGSIN (2)—Distribution in Tissues

MEGSIN was analyzed by Northern blot as follows. RNA was isolated from human mesangial cultured cells. Poly $(A)^+$ RNA (5 μg) from the cultured cells was separated by 1% agarose gel containing 2.2 M formamide, and transferred onto a nitrocellulose filter. The filter was hybridized in Rapid Hyb solution (Amersham, Arlington Heights, Ill.). The blot was washed at 60° C. with final stringency of 0.1×SSPE/ 0.1% SDS.

Northern blots of multiple human tissues and of human cancer cell lines were purchased from Clontech (Palo Alto, Calif.). Northern blot of multiple human tissues includes each 2 μg of poly $(A)^+$ RNA from heart, brain, placenta, lung, liver, skeletal muscle, kidney, and pancreas. Northern blot of human cancer cell lines includes each 2 μg of poly $(A)^+$ RNA derived from promyelocytic leukemia HL-60, Hela cell S3, chronic myeloid leukemia K-562, lymphoblastic leukemia MOLT-4, Burkitt's lymphoma Raji, adenocarcinoma of the large intestine SW480, lung cancer A549, and melanoma G361. Hybridization and washing were conducted in the same manner as described above.

Figure 3:
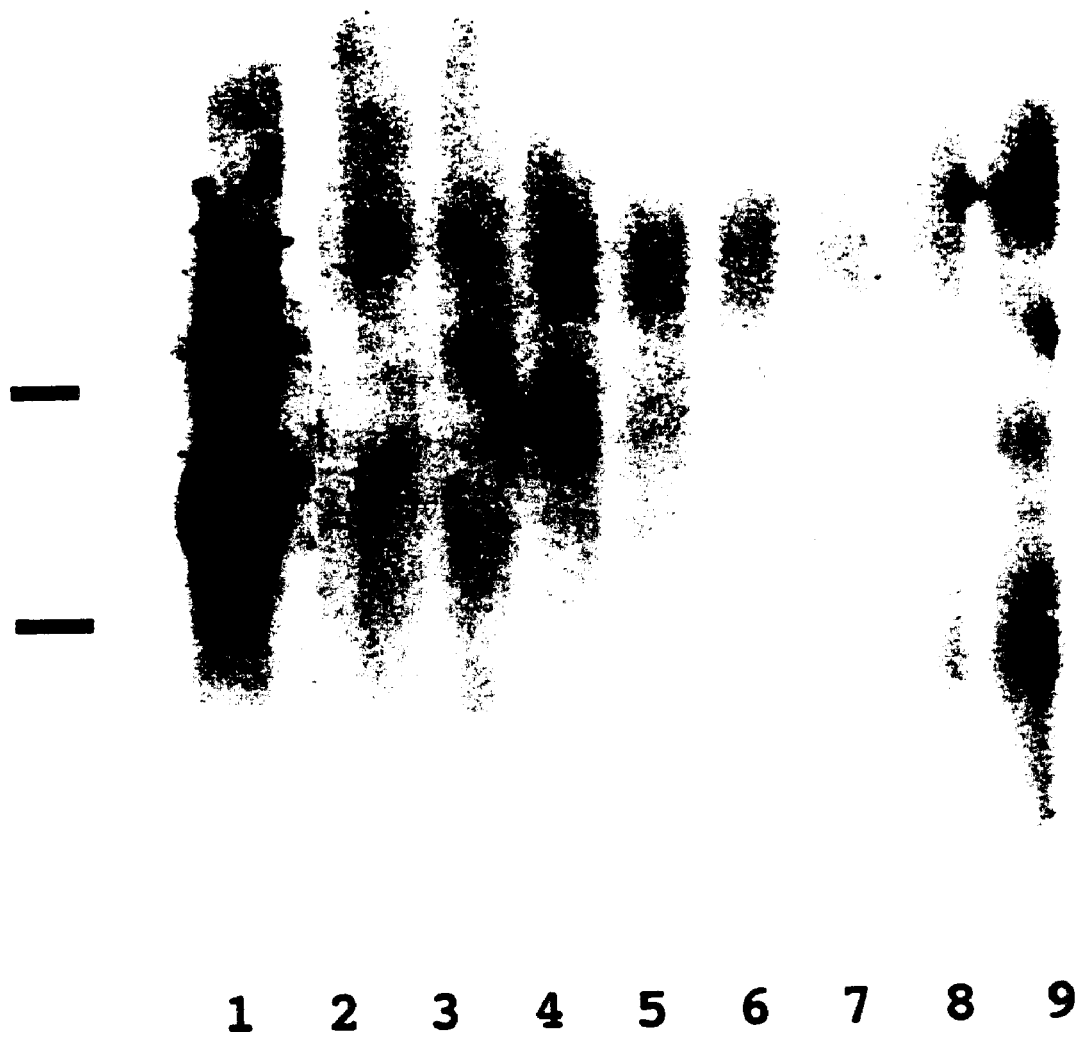
FIG. 3 shows the detected MEGSIN transcript by Northern blot analysis. Lane 1 represents mesangial cells, lane 2 promyelocytic leukemia HL-60, lane 3 Hela cells S3, lane 4 chronic myeloid leukemia K-562, lane 5 lymphoblastic leukemia MOLT-4, lane 6 Burkitt's lymphoma Raji, lane 7 adenocarcinoma of the large intestine SW480, lane 8 lung cancer A549, and lane 9 melanoma G361. The experiment was conducted as follows. Human Multiple Northern Blot containing 2 μg each of poly (A)$^+$RNA derived from heart, brain, placenta, lung, liver, skeletal muscle, kidney, and spleen (Clontech, CA, USA) and Human Cancer Cell Lineage Northern Blot containing 2 μg each of poly (A)$^+$RNA derived from promyelocytic leukemia HL-60, Hela cell S3, chronic myeloid leukemia K-562, lymphoblastic leukemia MOLT-4,Burkitt's lymphoma Raji, adenocarcinoma of the large intestine SW480, lung cancer A549, and melanoma G361 (Clontech, CA, USA) were used. RNA was isolated from human mesangial cultured cells, and poly (A)+RNA (2 μg) was separated by 1% agarose gel containing 2.2 M formamide, and transferred onto the blotting filter described above. The filter was hybridized in "Rapid Hyb solution (Amersham)" and washed at 60° C. to achieve final stringency of 0.1×SSPE/0.1% SDS.

Single transcript was detected in mesangial cultured cells by Northern blot analysis using MEGSIN cDNA probe, but was not detected in other organs or cell lines (FIG. 3). MEGSIN transcript was not detected in poly $(A)^+$ RNA derived form human kidney. This may be because kidney comprises endothelial cells, epithelial cells, and various other cells, and less mesangial cells.

Figure 4:
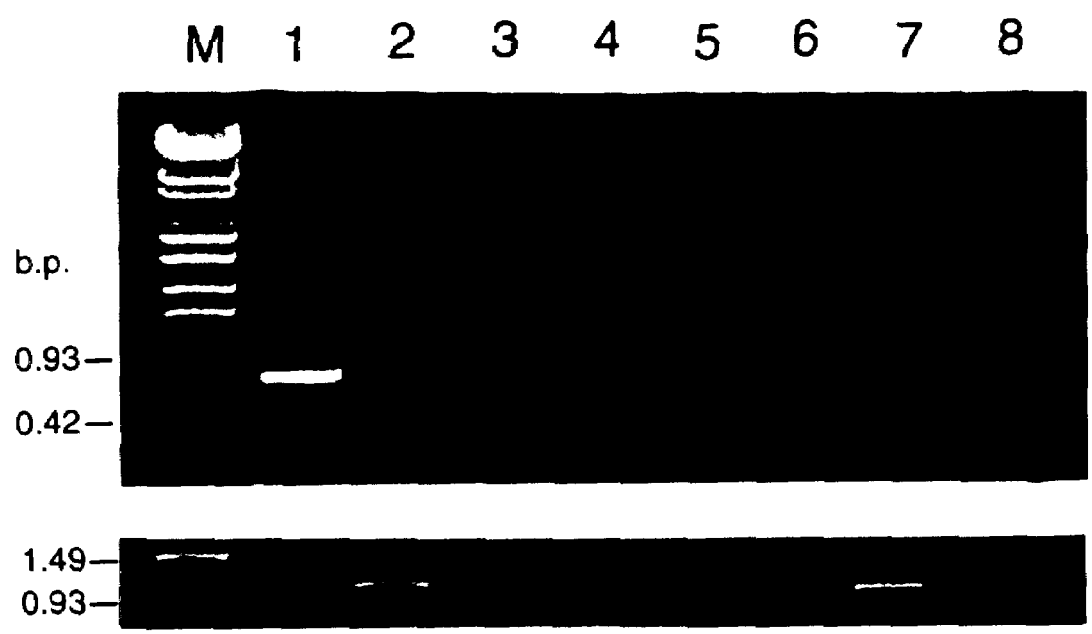
FIG. 4 is a photograph showing the result of RT-PCR. Lane 1 represents mesangial cell, lane 2 smooth muscle cell. lane 3 fibroblast, lane 4 endothelial cell, lane 5 renal epithelial cell, lane 6 keratinocyte, lane 7 monocyte. and lane 8 polymorphonuclear leukocyte (the upper photograph). The total RNA was isolated from human cultured cells, and reverse transcription was conducted using "T-Primed-First-Strand" kit (Pharmacia Biotech). Amplification by PCR was carried out with 25 cycles using DNA Thermal Cycler (Perkin Elmer). Each cycle was composed of denaturation at 94° C. for 1 mm, annealing at 60° C. for 2 mm, and extension at 72° C. for 2 mm using oligonucleotide primers of MEGSIN: sense 5'-ATGATCTCAGCAT-TGTGAATG-3'/SEQ ID NO: 16 and antisense 5'-ACT-GAGGGAGTTGCTTTTCTAC-3'/SEQ ID NO: 17. The estimated size of amplified fragment was 773 bp. In order to compare RNA level among different samples, β actin was used as the RNA internal control (the lower photograph). The PCR product was separated by electrophoresis on 1% agarose gel.

Actually, MEGSIN transcript was amplified from renal tissues by RT-PCR. RT-PCR was conducted using total RNA isolated from human cultured cells as a template, with "T-primed-First-Strand Kit" (Pharmacia Biotech). PCR amplification was performed under the condition with 25 cycles of 94° C. for 1 min, 60° C. for 2 min, and 72° C. for 2 min using "DNA Thermal Cycler" (Perkin Elmer Cetus). "5'-ATGATCTCAGCATTGTGAATG-3'/SEQ ID NO: 16" and "5'-ACTGAGGGAGTTGCTTTTCTAC-3'/SEQ ID NO: 17" were used as a sense primer and an antisense primer, respectively. The estimated size of the amplified fragment was 773 bp. In order to compare RNA level among different samples, β-actin was used as an internal RNA control. The PCR products were separated by 1% agarose gel electrophoresis. MEGSIN transcript was not amplified from human fibroblasts, smooth muscle cells, endothelial cells, epithelial cells, or keratinocyte, by RT-PCR (FIG. 4).

It is known that cultured mesangial cells acquire new phenotypes when activated and/or proliferate (R. J. Johnson et al., J. Am. Soc. Nephrol. 2 (10 Suppl.), S190, 1992; and J. Floege et al., Kidney Int. 45, 360, 1994). Therefore, MEGSIN expression may be enhanced to the detectable level by Northern blot analysis only when mesangial cells are activated and/or proliferate. The result of in situ hybridization for human renal tissues (described below) met this hypothesis.

EXAMPLE 9

Figure 5A:
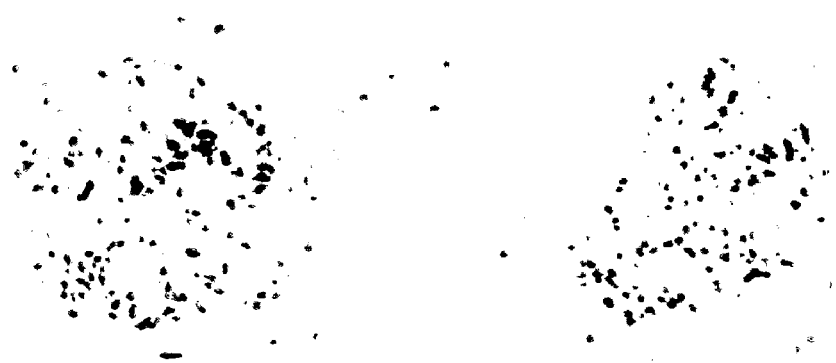
FIG. 5 is a photograph showing the result of in situ hybridization, indicating the expression of MEGSIN in mesangial cells in glomeruli from the normal subjects and IgA nephropathy patients. Panel (A) shows two glomeruli of IgA-N patients (40× magnification). MEGSIN signal was not observed in the uriniferous tubule or mesangial region. Panel (B) is the same photograph of 80× magnification. MEGSIN signal was observed in mesangial region of IgA-N patients. Panel (C) is the same photograph of 200× magnification, showing that mesangial cells are MEGSIN positive but endothelial cells and Bowman's capsule cells are MEGSIN negative.
Figure 5B:
Figure 5C:

Function Analysis of MEGSIN (3)—Comparison of Expression Level Between IgA Nephropathy Patients and Normal People Expression of MEGSIN mRNA was examined in human renal tissues obtained from 18 IgA nephropathy (IgA-N) patients and 3 normal subjects by in situ hybridization. In situ hybridization was conducted in the same manner as described above (Kidney Int. 52, 111, 1997). The nucleotide sequence of the nucleotide residues 391st to 428th of human MEGSIN cDNA was used as a probe. IgA-N patients were divided into 2 groups: patients whose mesangial proliferation was active, but glomerulosclerosis was weak (proliferative phase, n=9), and the others whose 30% or more of glomerulus was sclerosed (sclerotic phase, n=9). MEGSIN mRNA was detected exclusively in glomeruli both in normal subjects and IgA-N patients (FIG. 5A). MEGSIN transcript was localized in mesangial cells in the glomeruli (FIG. 5B and FIG. 5C). The pretreatment with RNase prior to hybridization for evaluating signal specificity resulted in the removal of most signals detected by the MEGSIN probe. The competitive experiment using 100 times excessive homologous or unrelating unlabeled oligonucleotides showed that MEGSIN signal disappeared by homologous oligonucleotide competitors, but not by non-homologous oligonucleotides. To quantify expression of MEGSIN mRNA, all nuclei in at least 10 glomeruli selected randomly and the nuclei comprising positive cytoplasm around them (cross section of vessel pole) were counted as blind test to calculate a percentage of the positive cells of whole nuclei. Mann-Whitney U test was used for statistical comparison. The number of MEGSIN positive cells in IgA-N during proliferative phase was significantly higher than that in kidneys of the normal subjects. These findings confirmed the hypothesis proposed by the present inventors that the expression of MEGSIN is enhanced by the activation and/or proliferation of mesangial cells.

EXAMPLE 10

Figure 6:
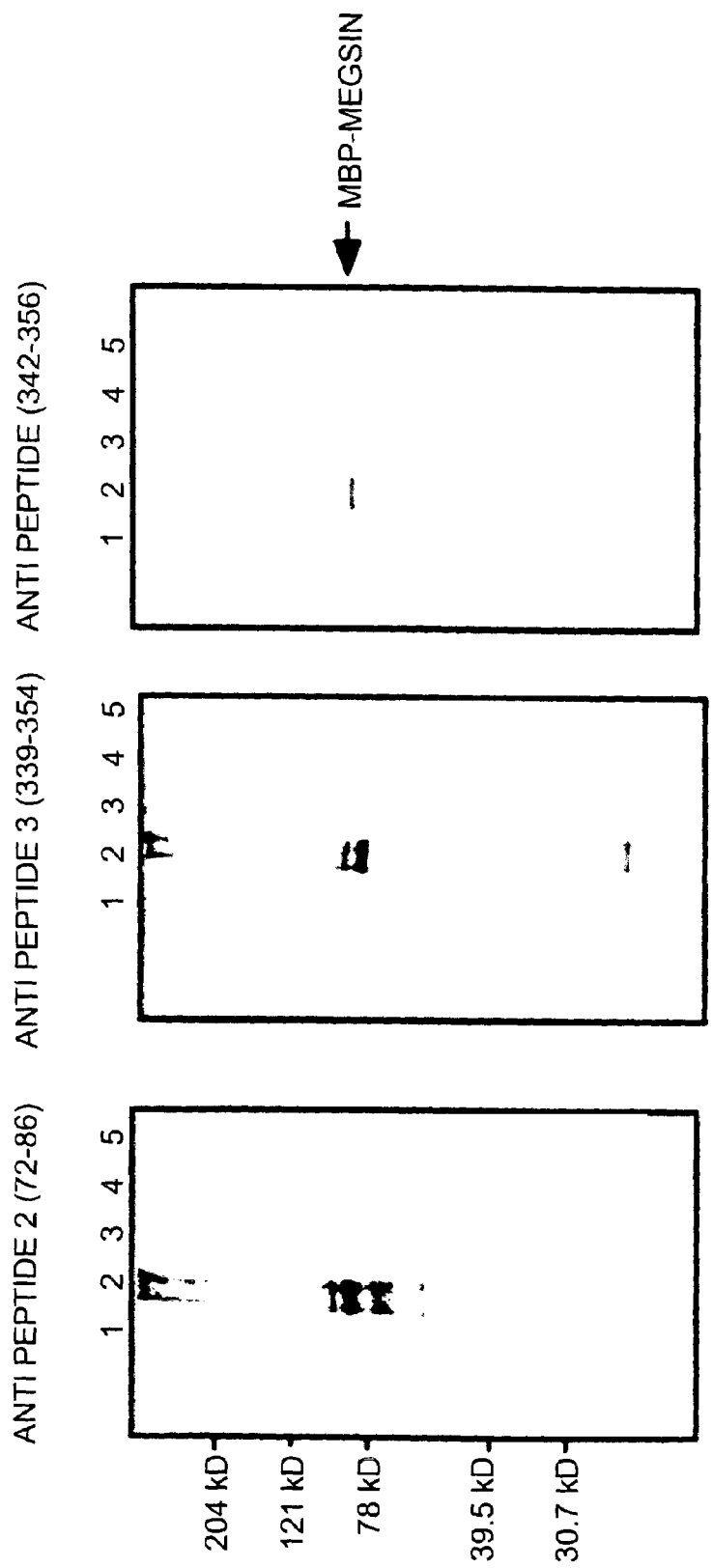
FIG. 6 shows the result of Western blotting using the polyclonal antibody specific to MEGSIN of the present invention. Lane 1 represents MBP, lane 2 MBP-MEGSIN fusion protein, lane 3 MBP-PAI II fusion protein, lane 4 PAI-I, and lane 5 albumin.

Production of Anti-MEGSIN Antibody (1) Production of Polyclonal Antibody Against Synthetic Peptide of MEGSIN Polyclonal antibodies against MEGSIN were produced using the region comprising low homology with other members of SERPIN family and hydrophilicity. Peptide "$H_2N$-C-S-N-I-V-E-K-Q-L-P-Q-S-T-L-F-R-COOH/SEQ ID NO: 18" comprising cysteine at the N end of 342nd to 356th peptides from the N end of MEGSIN protein was synthesized by solid phase peptide method, purified by high performance liquid chromatography, and bound to keyhole limpet hemocyanine (KLH) using m-maleimidobenzoyl-N-hydroxylsuccinimidoester (MBS). A rabbit was intracutaneously immunized with KLH binding peptide mixed with Freund's complete adjuvant (200 µg/individual). The rabbit was additionally immunized with KLH binding peptide mixed with Freund's incomplete adjuvant (200 µg peptide/individual) as a booster 2, 4, and 6 weeks after priming. To evaluate reactivity of sera from the blood collected after 44, 59, and 64 days with a synthetic peptide, enzyme-linked immunosorbent assay (ELISA) was conducted. The synthetic peptide was coated on a 96-well microplate (1 µg/well), washed, and blocked with bovine serum albumin. Reactivity of the antibodies in samples of sera with various dilution ratios was determined using HRP-conjugated goat anti-rabbit IgG as a secondary antibody and O-phenylenediamine as a substrate. Absorbance was measured at 492 nm after termination of the reaction. Antibody titer was increased by 6,800, 20,500, and 25,400 times after 44, 59, and 64 days. The obtained antibody was reacted with the MEGSIN fusion protein by Western blot, demonstrating specificity to MEGSIN protein. FIG. 6 shows the result of Western blot (anti peptide 342-356).

(2) Production of Polyclonal Antibodies Against Synthetic Peptide of MEGSIN

Polyclonal antibodies against MEGSIN was produced using the resign comprising low homology with other members of SERPIN family and hydrophilicity in the same manner as in (1). Peptide (1) "$H_2N$-C-F-R-E-M-D-D-N-Q-G-N-G-N-V-F-F-COOH/SEQ ID NO: 19" comprising cysteine at the N end of peptide 16th to 30th from the N end of MEGSIN protein, Peptide (2) "$H_2N$-C-S-Q-S-G-L-Q-S-Q-L-K-R-V-F-S-D-COOH/SEQ ID NO: 20" comprising cysteine at the N end of peptide 72nd to 86th, and Peptide (3) "$H_2N$-A-T-G-S-N-I-V-E-K-Q-L-P-Q-S-T-L-C-COOH/SEQ ID NO: 21" comprising cysteine at the C end of peptide 339th to 354th from the N end were synthesized by solid phase peptide method. These peptides were bound to bovine thyroglobulin (Sigma) using N-(6-maleimidocaproyloxy) succinimide (EMCS, Dojin Kagaku Kenkyu-syo (Dojindo)), dialyzed against 0.85% NaCl, and mixed well with adjuvant for emulsification, and subcutaneously administered to a rabbit. Three weeks after priming (20 µg/individual), the second immunization (50 µg/individual) was performed, and further four immunizations (50, 50, 100, 200 µg/individual) were conducted every other week. Freund's complete adjuvant (Difco) was used only for priming, and Freund's incomplete adjuvant (Difco) was used for the rest. Antibody titer in the serum obtained by the blood collection was evaluated by ELISA after 41 and 55 days.

The serially diluted antiserum (100 µl) was added to each well of the 96 well microplate coated with 50 ng/well of antigen for the first reaction, washed, and reacted with HRP conjugated goat anti-rabbit IgG (Meneki-kagaku Kenkyu-syo (Immunochemistry Institute)) as the second reaction. After washing, orthophenylenediamine (Wako Pure Chemical Industries) was used as a substrate for coloring, and absorbance was measured at 492 nm (SPECTRAmax 250, Molecular Devices).

As a result, antibody titer was increased by 6,400 and 51,200 times for peptide (A) and peptide (B), respectively 55 days after the additional immunization. Antibody titer of peptide (C) was increased 102,400 and 204,800 times 41 and 55 days after the additional immunization, respectively. Each of the obtained antibodies was confirmed to react with MBP-MEGSIN fusion protein by Western blot, demonstrating specificity to MEGSIN protein. FIG. 6 shows the result (peptide 2: 72-86, peptide 3: 339-354). The reaction specific to MBP-MEGSIN fusion protein was observed.

(3) Production of Polyclonal Antibody Against MBP-MEGSIN

The concentrated fusion protein MBP-MEGSIN (10 mM sodium phosphate, 0.5 M NaCl, and 10 mM maltose) obtained in Example 6 was mixed with the same volume of Freund's complete adjuvant and emulsified well. This emulsion (0.5 ml) was subcutaneously administered to a New Zealand White rabbit (female, about 4000 g) (20 µg/animal). The rabbit was additionally immunized with MBP-MEGSIN mixed with Freund's incomplete adjuvant, 3 weeks (50 µg/animal), 5 weeks (50 µg/animal), 7 weeks (50 µg/animal), 9 weeks (100 µg/animal), and 11 weeks (200 µg/animal) after priming. One week after third immunization, the blood sample was experimentally collected to measure antibody titer, resulting in increase of 204,800 times. The measurement of antibody titer was conducted by EIA using the 96 well-plate fixed with 50 ng/well antigen. Serially diluted antiserum (100 µg) was added to each well to conduct the first reaction, and the supernatant was removed. The plate was washed, reacted with anti-rabbit IgG Fab'-HRP (IBL, Japan), washed again, and measured by coloring with OPD (Sigma, USA). The obtained antiserum was confirmed to react specifically with MBP-MEGSIN by Western blot.

(4) Production of Monoclonal Antibody Against MBP-MEGSIN

The concentrated fusion protein MBP-MEGSIN (10 mM sodium phosphate, 0.5 M NaCl, and 10 mM maltose) obtained in Example 6 was mixed with the same volume of Freund's complete adjuvant and sufficiently emulsified. This emulsion was subcutaneously and intracutaneously administered to three 7 week-old Balb/c mice with 27G injection needles. The mice were immunized using Freund's incomplete adjuvant further 4 times every 7 days (the first immunization: 20 µg/mouse, the second to forth: 10 µl g/mouse). After four immunizations, a small amount of blood was collected from the tail vein for measuring antibody titer by EIA using the immunoplate coated with 50 ng/well antigen.

Accordingly, the splenic cells of the mice were fused with myeloma cell line X-63 Ag8 by the standard method using PEG. Monoclonal antibody producing hybridoma specific to immunogen can be selected by screening using EIA with the 96-well plate coated with immunogen, MBP, BSA, etc.

EXAMPLE 11

Production of Monoclonal Antibody Against MEGSIN (1) Production of Monoclonal Antibody Against His-Tag-MEGSIN (a) Expression of His-Tag-MEGSIN To obtain the gene comprising the coding region, total RNA was collected from human cultured mesangial cells using ISOGEN (Nippon Gene). cDNA was synthesized using Super Script II (GIBCO) as a reverse transcriptase. Using a part of this cDNA as a template, primers were designed so as to encode the coding region, that is, the primer EX-MEG1-2 comprising the initiation codon and the recognition sequence of restriction enzyme BamHI added at the 5' end (5'-ATCGGATCCATGGCCTCCCTTGCTG-CAGCAAATGCAGA-3'/SEQ ID NO: 22) and the primer EX-MEG2-2 comprising the stop codon and the HindIII recognition sequence (5'-ATAAGCTTTCAT-CAAGGGCAAGAAACTTTGCCACTGAATAAG-3'/SEQ ID NO: 23). PCR reaction was conducted using these primers and LA Taq (TaKaRa).

Reaction was performed in the reaction mixture containing 2.5 µl of 10×LA Taq buffer, 4 µl of dNTP mixture (2.5 mM), 2.5 µl of 25 mM magnesium chloride, 1 µl each of 20 µM PCR primers EX-MEG1-2 and EX-MEG2-2, 2.5 units of LA Taq, and cDNA, which was made up to 25 µl with sterilized water.

Each reagent was set on Gene Amp PCR System 9700 (Applied Biosystems) and reacted under the condition with 35 cycles of 96° C. for 1 min, 60° C. for 30 sec, and 72° C. for 2 min after heating at 96° C. for 3 min.

After the completion of reaction, PCR product was collected, treated with restriction enzymes BamHI (Takara) and HindIII (Takara), and subcloned to pUC18 with Ligation Kit ver. I (Takara). This plasmid was cultured in a small scale, collected with Wizard Plus Miniprep DNA Purification System (Promega) to confirm the gene sequence, and digested with BamHI and HindIII again to insert into multi cloning site in ptrcHisA (Invitrogen), a vector for protein expression, using Ligation Kit ver. I to obtain ptrcHisA-MEGSIN.

The prepared plasmid was transformed into *E. coli* JM 109, cultured on LB agar medium with 100 µg/ml ampicillin to select ampicillin resistant cells, cultured in 20 ml of LB medium with 100 µg/ml ampicillin at 37° C. overnight with shaking, and further cultured in 20 L of LB medium with 100 µg/ml ampicillin at 37° C. for 3 to 4 hours with shaking. When the absorbance was about 0.5 OD (A600) (Shimadzu, BIOSPEC-1600), isopropyl-beta-D-thiogalactoside (IPTG: Takara) was added to the final concentration of 1 mM, and cultured at 37° C. for 3 hours with shaking. The cells were collected by centrifugation, and washed with PBS. The expressed protein was collected using Ni-NTA Spin Kits (QIAGEN). The detail is as follows.

The sample was suspended in 50 ml of Buffer A (6M GuHCl, 0.1 M Na-phosphate, and 0.01 M Tris-HCl, pH 8.0), stirred for 1 hour at room temperature, and centrifuged at 10000 g for 15 min at 4° C. to collect the supernatant. To this supernatant, 8 ml of Ni-NTA previously equilibrated with Buffer A was added, stirred for 1 hour at room temperature, and transferred to the column. The column was washed with 80 ml of Buffer A, washed with 20 ml of Buffer B (8M Urea, 0.1 M Na-phosphate, and 0.01 M Tris-HCl, pH 8.0), and eluted with 20 ml of Buffer C (8M Urea, 0.1 M Na-phosphate, and 0.01 M Tris-HCl, pH 6.3). After the expressed protein was collected in the above manner, the eluted fraction was confirmed by SDS-PAGE. The positive fraction was separated by SDS-PAGE and stained with CBB to extract the target band. The extracted band was immersed in Protein Extraction Buffer to elute the protein.

(b) Production of Monoclonal Antibody Against His-Tag-MEGSIN

The MEGSIN fusion protein was mixed with the same volume of Freund's complete adjuvant, and emulsified well. The emulsion was subcutaneously and intracutaneously injected to three 7-week old Balb/c mice with the 27G injection needle. The mice were further immunized 4 times using Freund's incomplete adjuvant every 7 days after priming. The amounts of antigen applied were 20 µg/mouse for the first immunization and 10 µg/mouse for the second to forth. A small amount of blood was collected from the tail vein, and antibody titer was measured after the four immunizations. Antibody titer was assayed by ELISA using the 96-well plate coated with the 50 ng/well antigen. Accordingly, the mouse splenic cell was fused with myeloma cell line X-63 Ag8 by the standard method using PEG, and screened by ELISA using the 96-well plate coated with His-Tag-MEGSIN, histidine, or BSA, or Western blot. Monoclonal antibody producing hybridoma specific to immunogen was thus selected.

EXAMPLE 12

Measurement of MEGSIN in Urine by ELISA

Figure 7:
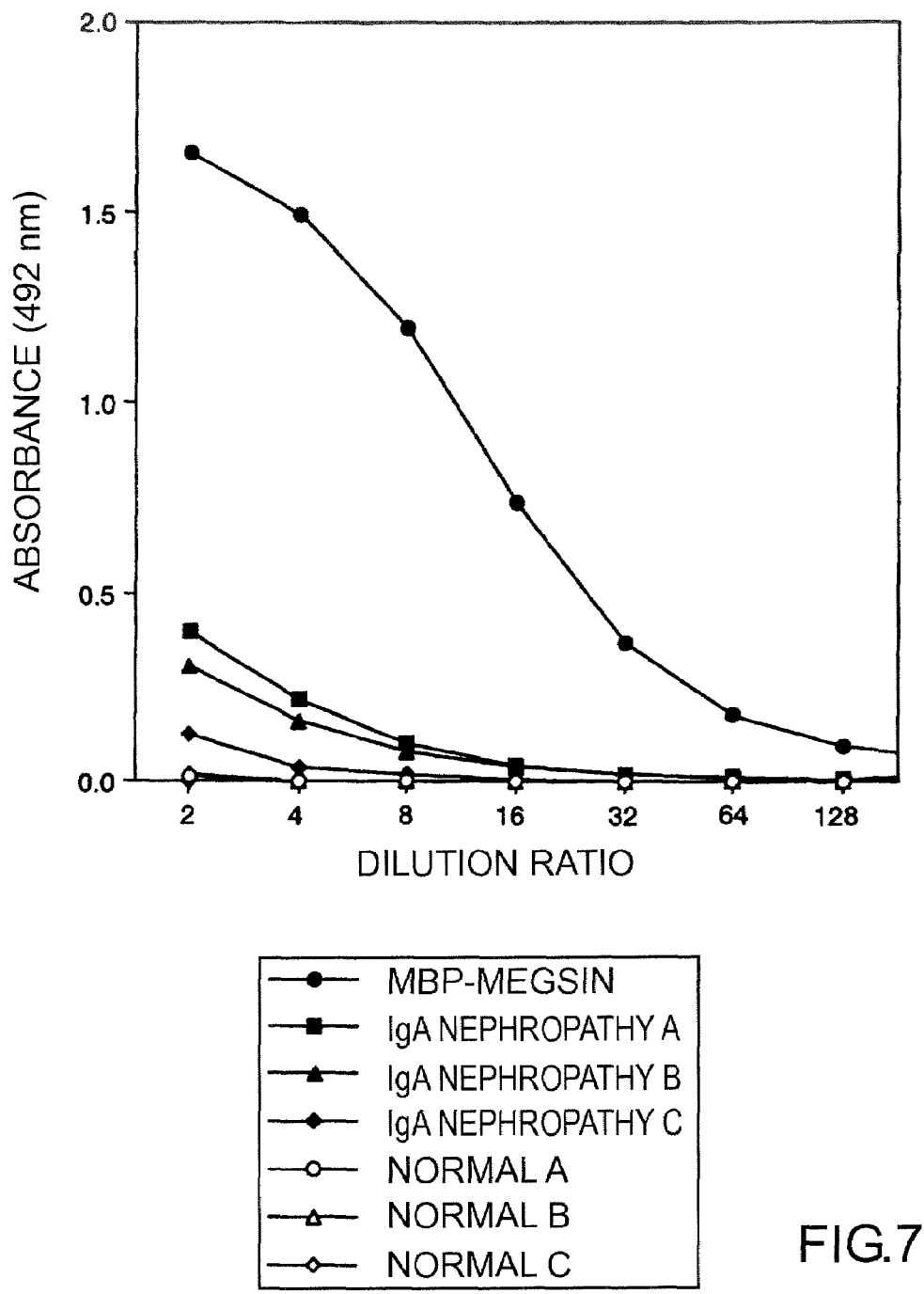
FIG. 7 is a graph showing MEGSIN measured by ELISA in the urine samples. The ordinate shows absorbance at 492 nm, and the abscissa shows the dilution ratio of the urine samples. MEGSIN was not detected in the normal subjects (-○-, -△-, and -◇-), but detected in the urine from IgA nephropathy patients (-■-, -◆- and -▲-) and MBP-MEGSIN (-●-).

Urine was collected from the IgA nephropathy patient and centrifuged. The obtained supernatant was concentrated using a ultrafilter for centrifugation (Millipore, Ultrafree, molecular weight cutoff: 5000). Stepwise diluted MBP-MEGSIN or concentrated urine (50 µl) was added into each well of the 96-well plate for ELISA coated with rabbit polyclonal anti-MEGSIN antibody (IgG fraction), kept at 4° C. overnight, washed with PBS (−), and blocked with Blockace (Dainippon Pharmaceutical Co., Ltd.). The plate was washed with PBS (−) containing 0.05% (w/v) Tween 20 (Tween-PBS). The biotin-labeled rabbit polyclonal anti-MEGSIN antibody was added to the plate, and kept at room temperature for 1 hour, and washed with Tween-PBS. The peroxidase-labeled streptoavidin solution (Amersham) (100 ml/well) was added to each well and washed with Tween-PBS, and 100 ml of orthophenylenediamine coloring substrate solution (Wako Pure Chemical) was added to each well. The reaction was conducted for 10 to 30 min in the dark at room temperature, and 50 ml of 2M sulfuric acid was added to each well to stop the reaction. The absorbance (492 nm) was measured by the microplate reader (SPECTRAmax 250, Molecular Devices) to determine MEGSIN concentration in the urine from calibration curve of a standard solution. The result is shown in FIG. 7. MEGSIN was detected in the urine from the IgA nephropathy patients.

EXAMPLE 13

Cloning of Rat MEGSIN cDNA (1) Cloning of cDNA by Degenerate PCR

Using ISOGEN (Nippon Gene) and oligotex, mRNA was extracted from the rat cultured mesangial cells of the 14th passage. This mRNA was subjected to reverse transcription reaction with reverse transcriptase Super Script II (GIBCO), and the obtained cDNA was used as a template. Based on the cDNA of human MEGSIN, the degenerate primers FY: GTGAATGCTGTGTACTTAAAGGCAANTGN/SEQ ID NO: 24 (corresponding to 172VNAVYFKGK180) and R21: AANAGRAANGGRTCNGC/SEQ ID NO: 25 (R is A or G, corresponding to 357ADHPFLF363) were prepared for the PCR under the condition with 35 cycles of 94° C. for 45 sec (denaturation), 50° C. for 45 sec (annealing), and 72° C. for 2 min (extension) using DNA Thermal Cycler (Perkin Elmer Cetus).

PCR product having the size similar to the expected size (576 bp) was inserted into pCRII vector (Clontech) and sequenced by dideoxy method using a DNA automatic sequencer.

The primers specific to the gene were prepared from the clone fragment of rat MEGSIN, and degenerate PCR was conducted again for obtaining the 5' region of rat MEGSIN.

First, the degenerate primer RM-CtermC1: ATGGCNTC-NGCNGCNGCNAAYGC/SEQ ID NO: 26 (Y is T or C), which corresponds to N-terminus of the sequence encoding human MEGSIN, and the reverse primers specific to rat MEGSIN, RM-MR-A2: CGACCTCCAGAGGCAATTC-CAGAGAGATCAGCCCTGG/SEQ ID NO: 27 and RM-MR-A1: GTCTTCCAAGCCTACAGATTTCAAGTG-GCTCCTC/SEQ ID NO: 28, were prepared. PCR was conducted with RM-CtermC1 and RM-MR-A2 under the condition with 45 cycles of 94° C. for 45 sec, 55° C. for 45 sec, and 72° C. for 1 min. Using the obtained PCR product as a template, nested PCR was conducted under the condition with 25 cycles of 94° C. for 45 sec, 55° C. for 45 sec, and 72° C. for 1 min, with RM-CtermC1 and RM-MR-A2. To enhance the amplification, PCR was further repeated using the same primers under the condition with 25 cycles of 94° C. for 30 sec, 55° C. for 30 sec, and 72° C. for 40 sec.

The obtained PCR product was inserted into pGEM-T-easy vector (Promega), and sequenced by dideoxy method using the DNA automatic sequencer.

(2) Cloning of cDNA by 5' RACE and 3' RACE Methods

The sequence completely comprising the open reading frame without mutation at the sites of initiation codon and stop codon of MEGSIN was determined. 5'-RACE and 3'-RACE methods were conducted by Marathon cDNA amplification kit (Clontech) using the primers designed based on the sequences obtained above in order to confirm the whole length sequence. For 5'-RACE, two types of gene specific antisense primers, RM-PR01: GCTCAGGGCAGT-GAAGATGCTCAGGGAAGA/SEQ ID NO: 29 and RM-PR02: CTGACGTGCACAGTCACCTCGAGCACC/SEQ ID NO: 30 were used. For 3'-RACE, the gene specific sense primer, RM-MR-S3: GAGGTCTCAGAAGAAGGCACT-GAGGCAACTGCTGCC/SEQ ID NO: 31 was used. Finally, based on the sequences obtained in such a manner, whole cDNA nucleotide sequence of rat MEGSIN composed of 1229 bp shown in SEQ ID NO: 3 was almost completely determined.

To obtain clones comprising open reading frame of the rat MEGSIN, two kinds of gene specific primers, RM-5' UTR-FS2: CTCTATAGGAGACACTTGG/SEQ ID NO: 32 (sense primer) and 3'-UTR-A1: GAAACAAATCAAAGCAAAC/SEQ ID NO: 33 (antisense primer), designed from the sequences obtained above, were used. PCR was conducted under the condition with 35 cycles of 94° C. for 45 sec (denaturation), 50° C. for 45 sec (annealing), and 72° C. for 1 min 30 sec (extension). The PCR product of the expected size (about 1300 bp) was inserted into pCRII vector to isolate the clones containing the open reading frame of rat MEGSIN.

EXAMPLE 14

Cloning of Mouse MEGSIN cDNA (1) Cloning of cDNA by PCR

Using ISOGEN (Nippon Gene), 10 µg of total RNA was extracted from mouse cultured mesangial cells of the 9th passage. From this RNA, first strand cDNA was synthesized using 20 pmol of oligo (dT) primer (Pharmacia) and 200 units of reverse transcriptase Super Script II (GIBCO) by reverse transcription reaction under the condition of 42° C. for 50 min and 70° C. for 15 min.

Based on the nucleotide sequences of human and rat MEGSIN, degenerate primers MF-1: 5'-GAAATTGAAAR-CAARCTGASYTTYCAGAAT-3'/SEQ ID NO: 34 (R is A or G, S is C or G, and Y is C or T), MF-2: 5'-CTGASYT-TYCAGAATCTAATGGAMTGGAC-3'/SEQ ID NO: 35 (S is C or G, Y is C or T, and M is A or C), and MR-4: 5'-GGAYTSAGGRAGTWGCTTTTCWACRATRTT-3'/SEQ ID NO: 36 (S is C or G, Y is C or T, M is A or C, and W is A or T), were prepared. PCR was conducted using MF-1 and MR-4 under the condition with 30 cycles with 94° C. for 1 min (denaturation), 60° C. for 1 min (annealing) and 72° C. for 30 sec (extension). Nested PCR was conduced using the obtained PCR product as a template and MF-2 and MR-4, under the same condition of the above to obtain the cDNA fragment of 300 bp.

(2) Extension of the 3' Region by RACE Method

Based on the sequences obtained above, the gene specific primers MMF3: 5'-GAGGTCTCAGAGGAGGGCACT-GAAGCCACTGCTGCC-3'/SEQ ID NO: 37 and MMF4: 5'-CCAGTGCAGATCTCTCTGGAATTGC-CTCTGGAGGTCGTC-3'/SEQ ID NO: 38 were prepared.

The new cDNA fragment of 127 bp was obtained by extending the 3'-region by RACE method (PCR: MMF4 and AP-1, nested PCR: MMF3 and AP-2) using 1.57 µg of poly (A)+ mRNA with Marathon cDNA Amplification Kit (CLONTECH).

(3) Extension of 5'-Region

Using 20 µg of total RNA and reverse transcriptase SuperScript II (GIBCO), the first strand DNA was synthesized. Using the gene specific primer MMR6: 5'-GCCTGT-TACTGTATAGGAAACCAAACCG-3'/SEQ ID NO: 39 and degenerate primer based on the nucleotide sequence of rat MEGSIN, DG-RMF1: 5'-ATGGCYTCCCTYGCT-GCWGCRAATGCAGARTTTKGC-3'/SEQ ID NO: 40 (Y is C or T, W is A or T, R is A or G, and K is G or T), PCR was conducted to obtain the new cDNA fragment of 5'-region of 720 bp, and the total of 1147 bp of cDNA nucleotide sequence (SEQ ID NO: 5) was determined. The deduced amino acid sequence based on the obtained cDNA nucleotide sequence (SEQ ID NO: 6) was compared with that of rat (SEQ ID NO: 4). The N-terminus region in the mouse amino acid sequence was coincident with the sequence of 13th or more of rat. This finding suggested that mouse cDNA comprising the translation initiation site at further 5' end.

EXAMPLE 15

Preparation of Transgenic Mouse (1) Preparation of pUC-MEGSIN

From the human cultured mesangial cells, mRNA was extracted by AGPC method. Using this as a template, RT-PCR was conducted with the sense primer 5' Bam-MEG: 5'-ATCGGATCCATGGCCTCCCTTGCT-3'/SEQ ID NO: 41 (containing BamHI restriction site) and the antisense primer 3' Hind-MEG: 5'-ATAAGCTTTCATCAT-CAAGGGCAAG-3' SEQ ID NO: 42 (containing Hind III restriction site) to amplify the full length open reading frame of MEGSIN.

The obtained PCR product was digested with BamHI and HindIII, and ligated with pUC 18 (Takara) digested with BamHI and HindIII to prepare pUC18 inserted with the full length open reading frame of MEGSIN (pUC-MEGSIN). The nucleotide sequence of MEGSIN inserted to pUC18 was confirmed by the dideoxytermination method.

(2) Construction of Gene

In order to add the oligonucleotide (5'-GCC GCC) to upstream of initiation codon in human MEGSIN cDNA, PCR was conducted under the following conditions to synthesize the 211 bp DNA.

Using pUC-MEGSIN obtained in (1) as a template, PCR was conduced with a set of sense primer B44F: 5'-ATG-GATCCGCCGCCATGGCCTCCCTTGCTG-CAGCAAATGCAGAG-3'/SEQ ID NO: 43 (containing BamHI site) and antisense primer H30-R: 5'-TATCCTGAG-GCAGTGTTAACAAGCAAC-3'/SEQ ID NO: 44 (containing HpaI site) using TaKaRa EX. Taq. (Takara). Salt was removed by ethanol precipitation, and the restriction site was prepared with BamHI and HapI to collect the 191 bp DNA fragment by the agarose gel electrophoresis.

From pUC-MEGSIN, the 3.5 kb fragment containing pUC18 using BamHI and HapI was obtained, and purified and collected by the agarose gel electrophoresis. By ligating this to the 191 bp DNA fragment of the above, the recombinant plasmid carrying human MEGSIN cDNA added with oligonucleotides, that is, pUC-New MEGSIN, was prepared, transformed to E. coli JM 109, and cloned. From pUC-New MEGSIN, the 1.2 kb fragment was collected using BamHI and HindIII through agarose gel electrophoresis. The ends of this fragment were blunted using TaKaRa Blunting Kit (Takara). pBsCAG-2 (constructed by introducing a SalI-PstI fragment obtained from pCAGGS into the SalI and PstI restriction sites of pBluescript II SK-) was digested with EcoRI to linearize, blunt-ended with TaKaRa Blunting Kit (Takara), and dephosphorylated by alkaline phosphatase (Takara). To this plasmid, the above described 1.2 kb fragment was ligated to prepare the recombinant plasmid, transformed to E. coli JM 109, and cloned. The clone in which the human MEGSIN cDNA was inserted in the same direction as chicken beta-actin promoter was selected by sequencing. This recombinant plasmid was named as pBsCAG-2/MEGSIN.

From pBsCAG-2/MEGSIN, the 3.4 kb DNA fragment was collected using SalI and NotI by the agarose gel electrophoresis.

(3) Preparation of Transgenic Mouse

To the pronucleus of fertilized egg of the mouse (B6C3F1 X C57/BL), 2 pl (2000 copies) of the DNA (3.4 kb) prepared in (2) was microinjected, and screening was performed by Southern hybridization described below.

Genomic DNA was prepared from the tail of the mouse using QIAGEN TISSUE KIT. Genomic DNA (2 μg) was completely digested with PstI, separated by the 0.8% agarose gel electrophoresis, and transferred to a nylon membrane. The DNA fragment of 1100 bp (extracted from pUC-MEGSIN with PstI and HindIII and collected by the agarose gel) was hybridized with the [32P]-dCTP labeled probe prepared by Random Primer DNA Labeling Kit Ver. 2 (Takara), at 68° C. for 2 hours.

The membrane was washed finally with 0.2×SSC/0.1% SDS, and autoradiographed.

The presence or absence of inserted DNA fragment and the number of copies were determined based on the appearance of the specific 1700 bp band. The direction of the inserted DNA fragment when multiple DNA fragments were inserted in tandem was determined by completely digesting 2 μg of genomic DNA with EcoRV followed by the same manipulation.

The obtained transgenic mice (F0) were crossed with the normal mice. The newborn mice were screened by the above method to obtain the transgenic mouse (F1). F2 mice were obtained By crossing transgenic mice comprising same heterozygous mutation (F1), and the transgenic mice comprising homozygous mutation were screened.

INDUSTRIAL APPLICABILITY

The present invention provides a DNA expressed specifically in mesangial cells, a protein encoded by the DNA, and an antibody binding to the protein. These are specific to mesangial cells, and useful for, for example, identifying mesangial cells, and detecting abnormalities in mesangial cells. Moreover, this protein would be helpful for clarifying the functions of mesangial cells and in turn, for investigating causes of diseases relating to mesangial cells. This invention is expectedly applicable to the treatment and diagnosis, of diseases relating to mesangial cells.

The invention claimed is:

1. A method for detecting mesangial proliferative nephropathy, the method comprising:

measuring an amount of protein that consists of the amino acid sequence of SEQ ID NO:2 contained in urine samples obtained from a patient suspected of suffering from mesangial proliferative nephropathy; and comparing the measured amount with that obtained from normal urine samples, wherein the higher protein level in the patient derived urine sample comparing with normal urine sample shows that the patient suffers from mesangial proliferative nephropathy.

* * * * *

SEQUENCE LISTING

```
<160> NUMBER OF SEQ ID NOS: 44

<210> SEQ ID NO 1
<211> LENGTH: 1143
<212> TYPE: DNA
<213> ORGANISM: Homo sapiens
<220> FEATURE:
<221> NAME/KEY: CDS
<222> LOCATION: (1)..(1140)

<400> SEQUENCE: 1 atg gcc tcc ctt gct gca gca aat gca gag ttt tgc ttc aac ctg ttc    48
Met Ala Ser Leu Ala Ala Ala Asn Ala Glu Phe Cys Phe Asn Leu Phe
 1               5                  10                  15
```

```
aga gag atg gat gac aat caa gga aat gga aat gtg ttc ttt tcc tct    96
Arg Glu Met Asp Asp Asn Gln Gly Asn Gly Asn Val Phe Phe Ser Ser
         20                  25                  30 ctg agc ctc ttc gct gcc ctg gcc ctg gtc cgc ttg ggc gct caa gat   144
Leu Ser Leu Phe Ala Ala Leu Ala Leu Val Arg Leu Gly Ala Gln Asp
     35                  40                  45 gac tcc ctc tct cag att gat aag ttg ctt cat gtt aac act gcc tca   192
Asp Ser Leu Ser Gln Ile Asp Lys Leu Leu His Val Asn Thr Ala Ser
 50                  55                  60 gga tat gga aac tct tct aat agt cag tca ggg ctc cag tct caa ctg   240
Gly Tyr Gly Asn Ser Ser Asn Ser Gln Ser Gly Leu Gln Ser Gln Leu
 65                  70                  75                  80 aaa aga gtt ttt tct gat ata aat gca tcc cac aag gat tat gat ctc   288
Lys Arg Val Phe Ser Asp Ile Asn Ala Ser His Lys Asp Tyr Asp Leu
                 85                  90                  95 agc att gtg aat ggg ctt ttt gct gaa aaa gtg tat ggc ttt cat aag   336
Ser Ile Val Asn Gly Leu Phe Ala Glu Lys Val Tyr Gly Phe His Lys
            100                 105                 110 gac tac att gag tgt gcc gaa aaa tta tac gat gcc aaa gtg gag cga   384
Asp Tyr Ile Glu Cys Ala Glu Lys Leu Tyr Asp Ala Lys Val Glu Arg
        115                 120                 125 gtt gac ttt acg aat cat tta gaa gac act aga cgt aat att aat aag   432
Val Asp Phe Thr Asn His Leu Glu Asp Thr Arg Arg Asn Ile Asn Lys
    130                 135                 140 tgg gtt gaa aat gaa aca cat ggc aaa atc aag aac gtg att ggt gaa   480
Trp Val Glu Asn Glu Thr His Gly Lys Ile Lys Asn Val Ile Gly Glu
145                 150                 155                 160 ggt ggc ata agc tca tct gct gta atg gtg ctg gtg aat gct gtg tac   528
Gly Gly Ile Ser Ser Ser Ala Val Met Val Leu Val Asn Ala Val Tyr
                165                 170                 175 ttc aaa ggc aag tgg caa tca gcc ttc acc aag agc gaa acc ata aat   576
Phe Lys Gly Lys Trp Gln Ser Ala Phe Thr Lys Ser Glu Thr Ile Asn
            180                 185                 190 tgc cat ttc aaa tct ccc aag tgc tct ggg aag gca gtc gcc atg atg   624
Cys His Phe Lys Ser Pro Lys Cys Ser Gly Lys Ala Val Ala Met Met
        195                 200                 205 cat cag gaa cgg aag ttc aat ttg tct gtt att gag gac cca tca atg   672
His Gln Glu Arg Lys Phe Asn Leu Ser Val Ile Glu Asp Pro Ser Met
    210                 215                 220 aag att ctt gag ctc aga tac aat ggt ggc ata aac atg tac gtt ctg   720
Lys Ile Leu Glu Leu Arg Tyr Asn Gly Gly Ile Asn Met Tyr Val Leu
225                 230                 235                 240 ctg cct gag aat gac ctc tct gaa att gaa aac aaa ctg acc ttt cag   768
Leu Pro Glu Asn Asp Leu Ser Glu Ile Glu Asn Lys Leu Thr Phe Gln
                245                 250                 255 aat cta atg gaa tgg acc aat cca agg cga atg acc tct aag tat gtt   816
Asn Leu Met Glu Trp Thr Asn Pro Arg Arg Met Thr Ser Lys Tyr Val
            260                 265                 270 gag gta ttt ttt cct cag ttc aag ata gag aag aat tat gaa atg aaa   864
Glu Val Phe Phe Pro Gln Phe Lys Ile Glu Lys Asn Tyr Glu Met Lys
        275                 280                 285 caa tat ttg aga gcc cta ggg ctg aaa gat atc ttt gat gaa tcc aaa   912
Gln Tyr Leu Arg Ala Leu Gly Leu Lys Asp Ile Phe Asp Glu Ser Lys
    290                 295                 300 gca gat ctc tct ggg att gct tcg ggg ggt cgt ctg tat ata tca agg   960
Ala Asp Leu Ser Gly Ile Ala Ser Gly Gly Arg Leu Tyr Ile Ser Arg
305                 310                 315                 320 atg atg cac aaa tct tac ata gag gtc act gag gag ggc acc gag gct  1008
Met Met His Lys Ser Tyr Ile Glu Val Thr Glu Glu Gly Thr Glu Ala
                325                 330                 335
```

```
act gct gcc aca gga agt aat att gta gaa aag caa ctc cct cag tcc         1056
Thr Ala Ala Thr Gly Ser Asn Ile Val Glu Lys Gln Leu Pro Gln Ser
        340                 345                 350 acg ctg ttt aga gct gac cac cca ttc cta ttt gtt atc agg aag gat         1104
Thr Leu Phe Arg Ala Asp His Pro Phe Leu Phe Val Ile Arg Lys Asp
    355                 360                 365 gac atc atc tta ttc agt ggc aaa gtt tct tgc cct tga                     1143
Asp Ile Ile Leu Phe Ser Gly Lys Val Ser Cys Pro
370                 375                 380

<210> SEQ ID NO 2
<211> LENGTH: 380
<212> TYPE: PRT
<213> ORGANISM: Homo sapiens

<400> SEQUENCE: 2

Met Ala Ser Leu Ala Ala Ala Asn Ala Glu Phe Cys Phe Asn Leu Phe
1               5                   10                  15

Arg Glu Met Asp Asp Asn Gln Gly Asn Gly Asn Val Phe Phe Ser Ser
                20                  25                  30

Leu Ser Leu Phe Ala Ala Leu Ala Leu Val Arg Leu Gly Ala Gln Asp
            35                  40                  45

Asp Ser Leu Ser Gln Ile Asp Lys Leu Leu His Val Asn Thr Ala Ser
        50                  55                  60

Gly Tyr Gly Asn Ser Ser Asn Ser Gln Ser Gly Leu Gln Ser Gln Leu
65                  70                  75                  80

Lys Arg Val Phe Ser Asp Ile Asn Ala Ser His Lys Asp Tyr Asp Leu
                85                  90                  95

Ser Ile Val Asn Gly Leu Phe Ala Glu Lys Val Tyr Gly Phe His Lys
            100                 105                 110

Asp Tyr Ile Glu Cys Ala Glu Lys Leu Tyr Asp Ala Lys Val Glu Arg
        115                 120                 125

Val Asp Phe Thr Asn His Leu Glu Asp Thr Arg Arg Asn Ile Asn Lys
    130                 135                 140

Trp Val Glu Asn Glu Thr His Gly Lys Ile Lys Asn Val Ile Gly Glu
145                 150                 155                 160

Gly Gly Ile Ser Ser Ala Val Met Val Leu Val Asn Ala Val Tyr
                165                 170                 175

Phe Lys Gly Lys Trp Gln Ser Ala Phe Thr Lys Ser Glu Thr Ile Asn
            180                 185                 190

Cys His Phe Lys Ser Pro Lys Cys Ser Gly Lys Ala Val Ala Met Met
        195                 200                 205

His Gln Glu Arg Lys Phe Asn Leu Ser Val Ile Glu Asp Pro Ser Met
    210                 215                 220

Lys Ile Leu Glu Leu Arg Tyr Asn Gly Gly Ile Asn Met Tyr Val Leu
225                 230                 235                 240

Leu Pro Glu Asn Asp Leu Ser Glu Ile Glu Asn Lys Leu Thr Phe Gln
                245                 250                 255

Asn Leu Met Glu Trp Thr Asn Pro Arg Arg Met Thr Ser Lys Tyr Val
            260                 265                 270

Glu Val Phe Phe Pro Gln Phe Lys Ile Glu Lys Asn Tyr Glu Met Lys
        275                 280                 285

Gln Tyr Leu Arg Ala Leu Gly Leu Lys Asp Ile Phe Asp Glu Ser Lys
    290                 295                 300

Ala Asp Leu Ser Gly Ile Ala Ser Gly Gly Arg Leu Tyr Ile Ser Arg
305                 310                 315                 320
```

```
Met Met His Lys Ser Tyr Ile Glu Val Thr Glu Gly Thr Glu Ala
            325                 330                 335

Thr Ala Ala Thr Gly Ser Asn Ile Val Glu Lys Gln Leu Pro Gln Ser
            340                 345                 350

Thr Leu Phe Arg Ala Asp His Pro Phe Leu Phe Val Ile Arg Lys Asp
            355                 360                 365

Asp Ile Ile Leu Phe Ser Gly Lys Val Ser Cys Pro
    370                 375                 380

<210> SEQ ID NO 3
<211> LENGTH: 1229
<212> TYPE: DNA
<213> ORGANISM: Rattus rattus
<220> FEATURE:
<221> NAME/KEY: CDS
<222> LOCATION: (8)..(1147)
<220> FEATURE:
<221> NAME/KEY: unsure
<222> LOCATION: (158)..(160), (287)..(289)
<223> OTHER INFORMATION: n is unknown.

<400> SEQUENCE: 3 tttcaaa atg gcc tcc ctt gct gca gca aat gca gaa ttt ggc ttc gac      49
        Met Ala Ser Leu Ala Ala Ala Asn Ala Glu Phe Gly Phe Asp
          1               5                  10 tta ttc aga gag atg gat agt agt caa gga aac gga aat gta ttc ttc      97
Leu Phe Arg Glu Met Asp Ser Ser Gln Gly Asn Gly Asn Val Phe Phe
 15                  20                  25                  30 tct tcc ctg agc atc ttc act gcc ctg agc cta atc cgt ttg ggt gct     145
Ser Ser Leu Ser Ile Phe Thr Ala Leu Ser Leu Ile Arg Leu Gly Ala
                 35                  40                  45 cga ggt gac tgt nnn cgt cag att gac aag gcc ctg cac ttt atc tcc     193
Arg Gly Asp Cys Xaa Arg Gln Ile Asp Lys Ala Leu His Phe Ile Ser
             50                  55                  60 cca tca aga caa ggg aat tca tcg aac agt cag cta gga ctg caa tat     241
Pro Ser Arg Gln Gly Asn Ser Ser Asn Ser Gln Leu Gly Leu Gln Tyr
         65                  70                  75 caa ttg aaa aga gtt ctt gct gac ata aac tca tct cat aag gat nnn     289
Gln Leu Lys Arg Val Leu Ala Asp Ile Asn Ser Ser His Lys Asp Xaa
 80                  85                  90 aaa ctc agc att gcc aat gga gtt ttt gca gag aaa gta ttt gat ttt     337
Lys Leu Ser Ile Ala Asn Gly Val Phe Ala Glu Lys Val Phe Asp Phe
 95                 100                 105                 110 cat aag agc tat atg gag tgt gct gaa aac tta tac aat gct aaa gtg     385
His Lys Ser Tyr Met Glu Cys Ala Glu Asn Leu Tyr Asn Ala Lys Val
                115                 120                 125 gaa aga gtt gat ttt aca aat gat ata caa gaa acc aga ttt aaa att     433
Glu Arg Val Asp Phe Thr Asn Asp Ile Gln Glu Thr Arg Phe Lys Ile
            130                 135                 140 aat aaa tgg att gaa aat gaa aca cat ggc aaa atc aag aag gtg ttg     481
Asn Lys Trp Ile Glu Asn Glu Thr His Gly Lys Ile Lys Lys Val Leu
        145                 150                 155 ggg gac agc agc ctc agc tca tca gct gtc atg gtg cta gtg aat gct     529
Gly Asp Ser Ser Leu Ser Ser Ser Ala Val Met Val Leu Val Asn Ala
    160                 165                 170 gtt tac ttc aaa ggc aag tgg aaa tcg gcc ttc acc aag agt gat acc     577
Val Tyr Phe Lys Gly Lys Trp Lys Ser Ala Phe Thr Lys Ser Asp Thr
175                 180                 185                 190 ctc agt tgc cat ttc agg tct ccc agc ggt cct gga aaa gca gtt aat     625
Leu Ser Cys His Phe Arg Ser Pro Ser Gly Pro Gly Lys Ala Val Asn
                195                 200                 205
```

```
atg atg cat caa gaa cgg agg ttc aat ttg tct acc att cag gag cca      673
Met Met His Gln Glu Arg Arg Phe Asn Leu Ser Thr Ile Gln Glu Pro
        210                 215                 220 cca atg cag att ctt gag cta caa tat cat ggt ggc ata agc atg tac      721
Pro Met Gln Ile Leu Glu Leu Gln Tyr His Gly Gly Ile Ser Met Tyr
                225                 230                 235 atc atg ttg ccc gag gat gac cta tcc gaa att gaa agc aag ctg agt      769
Ile Met Leu Pro Glu Asp Asp Leu Ser Glu Ile Glu Ser Lys Leu Ser
            240                 245                 250 ttc cag aat cta atg gac tgg aca aat agc agg aag atg aaa tct cag      817
Phe Gln Asn Leu Met Asp Trp Thr Asn Ser Arg Lys Met Lys Ser Gln
255                 260                 265                 270 tat gtg aat gtg ttt ctc ccc cag ttc aag ata gag aaa gat tat gaa      865
Tyr Val Asn Val Phe Leu Pro Gln Phe Lys Ile Glu Lys Asp Tyr Glu
                275                 280                 285 atg agg agc cac ttg aaa tct gta ggc ttg gaa gac atc ttt gtt gag      913
Met Arg Ser His Leu Lys Ser Val Gly Leu Glu Asp Ile Phe Val Glu
            290                 295                 300 tcc agg gct gat ctg tct gga att gcc tct gga ggt cgt ctc tat gta      961
Ser Arg Ala Asp Leu Ser Gly Ile Ala Ser Gly Gly Arg Leu Tyr Val
        305                 310                 315 tca aag cta atg cac aag tcc ctc ata gag gtc tca gaa gaa ggc acc     1009
Ser Lys Leu Met His Lys Ser Leu Ile Glu Val Ser Glu Glu Gly Thr
    320                 325                 330 gag gca act gct gcc aca gaa agt aac atc gtt gaa aag cta ctt cct     1057
Glu Ala Thr Ala Ala Thr Glu Ser Asn Ile Val Glu Lys Leu Leu Pro
335                 340                 345                 350 gaa tcc acg gtg ttc aga gct gac cgc ccc ttt ctg ttt gtc att agg     1105
Glu Ser Thr Val Phe Arg Ala Asp Arg Pro Phe Leu Phe Val Ile Arg
                355                 360                 365 aag aat ggc atc atc tta ttt act ggc aaa gtc tcg tgt cct              1147
Lys Asn Gly Ile Ile Leu Phe Thr Gly Lys Val Ser Cys Pro
            370                 375                 380 tgaaattcta tttggttttc catacactaa caggcatgaa gaaacatcat aagtgaatag   1207
aattgtaatt ggaagtacat gg                                            1229

<210> SEQ ID NO 4
<211> LENGTH: 380
<212> TYPE: PRT
<213> ORGANISM: Rattus rattus
<220> FEATURE:
<221> NAME/KEY: UNSURE
<222> LOCATION: 51, 94
<223> OTHER INFORMATION: Xaa is unknown.

<400> SEQUENCE: 4

Met Ala Ser Leu Ala Ala Ala Asn Ala Glu Phe Gly Phe Asp Leu Phe
 1               5                  10                  15

Arg Glu Met Asp Ser Ser Gln Gly Asn Gly Asn Val Phe Phe Ser Ser
                20                  25                  30

Leu Ser Ile Phe Thr Ala Leu Ser Leu Ile Arg Leu Gly Ala Arg Gly
            35                  40                  45

Asp Cys Xaa Arg Gln Ile Asp Lys Ala Leu His Phe Ile Ser Pro Ser
        50                  55                  60

Arg Gln Gly Asn Ser Ser Asn Ser Gln Leu Gly Leu Gln Tyr Gln Leu
65                  70                  75                  80

Lys Arg Val Leu Ala Asp Ile Asn Ser Ser His Lys Asp Xaa Lys Leu
                85                  90                  95
```

```
Ser Ile Ala Asn Gly Val Phe Ala Glu Lys Val Phe Asp Phe His Lys
            100                 105                 110
Ser Tyr Met Glu Cys Ala Glu Asn Leu Tyr Asn Ala Lys Val Glu Arg
        115                 120                 125
Val Asp Phe Thr Asn Asp Ile Gln Glu Thr Arg Phe Lys Ile Asn Lys
    130                 135                 140
Trp Ile Glu Asn Glu Thr His Gly Lys Ile Lys Lys Val Leu Gly Asp
145                 150                 155                 160
Ser Ser Leu Ser Ser Ala Val Met Val Leu Val Asn Ala Val Tyr
                165                 170                 175
Phe Lys Gly Lys Trp Lys Ser Ala Phe Thr Lys Ser Asp Thr Leu Ser
            180                 185                 190
Cys His Phe Arg Ser Pro Ser Gly Pro Gly Lys Ala Val Asn Met Met
        195                 200                 205
His Gln Glu Arg Arg Phe Asn Leu Ser Thr Ile Gln Glu Pro Pro Met
    210                 215                 220
Gln Ile Leu Glu Leu Gln Tyr His Gly Gly Ile Ser Met Tyr Ile Met
225                 230                 235                 240
Leu Pro Glu Asp Asp Leu Ser Glu Ile Glu Ser Lys Leu Ser Phe Gln
                245                 250                 255
Asn Leu Met Asp Trp Thr Asn Ser Arg Lys Met Lys Ser Gln Tyr Val
            260                 265                 270
Asn Val Phe Leu Pro Gln Phe Lys Ile Glu Lys Asp Tyr Glu Met Arg
        275                 280                 285
Ser His Leu Lys Ser Val Gly Leu Glu Asp Ile Phe Val Glu Ser Arg
    290                 295                 300
Ala Asp Leu Ser Gly Ile Ala Ser Gly Gly Arg Leu Tyr Val Ser Lys
305                 310                 315                 320
Leu Met His Lys Ser Leu Ile Glu Val Ser Glu Glu Gly Thr Glu Ala
                325                 330                 335
Thr Ala Ala Thr Glu Ser Asn Ile Val Glu Lys Leu Leu Pro Glu Ser
            340                 345                 350
Thr Val Phe Arg Ala Asp Arg Pro Phe Leu Phe Val Ile Arg Lys Asn
        355                 360                 365
Gly Ile Ile Leu Phe Thr Gly Lys Val Ser Cys Pro
    370                 375                 380

<210> SEQ ID NO 5
<211> LENGTH: 1147
<212> TYPE: DNA
<213> ORGANISM: Mus musculus
<220> FEATURE:
<221> NAME/KEY: CDS
<222> LOCATION: (1)..(1104)

<400> SEQUENCE: 5 ttc gac tta ttc aga gag atg gat agt agc caa gga aat gga aat gta        48
Phe Asp Leu Phe Arg Glu Met Asp Ser Ser Gln Gly Asn Gly Asn Val
  1               5                  10                  15 ttc ttc tct tcc ctg agc atc ttc act gcc ctg acc cta atc cgt ctg        96
Phe Phe Ser Ser Leu Ser Ile Phe Thr Ala Leu Thr Leu Ile Arg Leu
                 20                  25                  30 ggt gct cga ggt gac tgt gca cgt cag att gac aag gca ctg cac ttt       144
Gly Ala Arg Gly Asp Cys Ala Arg Gln Ile Asp Lys Ala Leu His Phe
             35                  40                  45
```

-continued

| | | |
|---|---|---|
| aac ata cca tca aga caa gga aac tca tct aat aat cag cca gga ctt<br>Asn Ile Pro Ser Arg Gln Gly Asn Ser Ser Asn Asn Gln Pro Gly Leu<br>    50                          55                          60 | 192 |
| cag tat caa ttg aaa aga gtt ctt gct gac ata aac tca tct cat aag<br>Gln Tyr Gln Leu Lys Arg Val Leu Ala Asp Ile Asn Ser Ser His Lys<br>65                      70                        75                        80 | 240 |
| gat tat gaa ctc agc att gcc act gga gtt ttt gca gaa aaa gtc tat<br>Asp Tyr Glu Leu Ser Ile Ala Thr Gly Val Phe Ala Glu Lys Val Tyr<br>                        85                        90                        95 | 288 |
| gac ttt cat aag aac tac att gag tgt gct gaa aac tta tac aat gct<br>Asp Phe His Lys Asn Tyr Ile Glu Cys Ala Glu Asn Leu Tyr Asn Ala<br>                    100                    105                    110 | 336 |
| aaa gtg gaa aga gtt gac ttc aca aat gat gta caa gat acc aga ttt<br>Lys Val Glu Arg Val Asp Phe Thr Asn Asp Val Gln Asp Thr Arg Phe<br>          115                    120                    125 | 384 |
| aaa att aat aaa tgg att gaa aat gag aca cat gga aag atc aag aag<br>Lys Ile Asn Lys Trp Ile Glu Asn Glu Thr His Gly Lys Ile Lys Lys<br>                    130                    135                    140 | 432 |
| gtg ttg ggc gac agc agc ctc agc tcg tcg gct gtc atg gtg ctg gtg<br>Val Leu Gly Asp Ser Ser Leu Ser Ser Ser Ala Val Met Val Leu Val<br>145                    150                    155                    160 | 480 |
| aac gct gtt tac ttc aaa ggc aaa tgg aaa tcg gcc ttc acc aag act<br>Asn Ala Val Tyr Phe Lys Gly Lys Trp Lys Ser Ala Phe Thr Lys Thr<br>                    165                    170                    175 | 528 |
| gat acc ctc agt tgc cgt ttt agg tct ccc acg tgt cct gga aaa gta<br>Asp Thr Leu Ser Cys Arg Phe Arg Ser Pro Thr Cys Pro Gly Lys Val<br>                      180                    185                    190 | 576 |
| gtt aat atg atg cat caa gaa cgg cgg ttc aat ttg tct acc att cag<br>Val Asn Met Met His Gln Glu Arg Arg Phe Asn Leu Ser Thr Ile Gln<br>          195                    200                    205 | 624 |
| cag cca cca atg cag gtt ctt gag ctc caa tat cat ggt ggc ata agc<br>Gln Pro Pro Met Gln Val Leu Glu Leu Gln Tyr His Gly Gly Ile Ser<br>                    210                    215                    220 | 672 |
| atg tac att atg ctg cct gag gat ggc cta tgt gaa att gaa agc aag<br>Met Tyr Ile Met Leu Pro Glu Asp Gly Leu Cys Glu Ile Glu Ser Lys<br>225                    230                    235                    240 | 720 |
| ctg agt ttc cag aat ctg atg gac tgg acc aat agg agg aaa atg aaa<br>Leu Ser Phe Gln Asn Leu Met Asp Trp Thr Asn Arg Arg Lys Met Lys<br>                    245                    250                    255 | 768 |
| tct cag tat gtg aac gtg ttt ctc ccc cag ttc aag ata gag aag aat<br>Ser Gln Tyr Val Asn Val Phe Leu Pro Gln Phe Lys Ile Glu Lys Asn<br>                    260                    265                    270 | 816 |
| tat gaa atg acg cac cac ttg aaa tcc tta ggc ttg aaa gat atc ttt<br>Tyr Glu Met Thr His His Leu Lys Ser Leu Gly Leu Lys Asp Ile Phe<br>          275                    280                    285 | 864 |
| gat gag tcc agt gca gat ctc tct gga att gcc tct gga ggt cgt ctc<br>Asp Glu Ser Ser Ala Asp Leu Ser Gly Ile Ala Ser Gly Gly Arg Leu<br>                    290                    295                    300 | 912 |
| tac gta tca aag cta atg cac aag tca ttc ata gag gtc tca gag gag<br>Tyr Val Ser Lys Leu Met His Lys Ser Phe Ile Glu Val Ser Glu Glu<br>305                    310                    315                    320 | 960 |
| ggc act gaa gcc act gct gcc aca gaa aat aac att gtt gaa aag cag<br>Gly Thr Glu Ala Thr Ala Ala Thr Glu Asn Asn Ile Val Glu Lys Gln<br>                    325                    330                    335 | 1008 |
| ctt cct gag tcc aca gtg ttc aga gcc gac cgc ccc ttt ctg ttt gtc<br>Leu Pro Glu Ser Thr Val Phe Arg Ala Asp Arg Pro Phe Leu Phe Val<br>                    340                    345                    350 | 1056 |

-continued

```
atc aag aag aat gac atc atc tta ttt act ggc aaa gtc tct tgt cct   1104
Ile Lys Lys Asn Asp Ile Ile Leu Phe Thr Gly Lys Val Ser Cys Pro
        355                 360                 365 tgaaattcga tttggtttcc tatacagtaa caggcatcaa gaa                   1147
```

<210> SEQ ID NO 6
<211> LENGTH: 368
<212> TYPE: PRT
<213> ORGANISM: Mus musculus

<400> SEQUENCE: 6

```
Phe Asp Leu Phe Arg Glu Met Asp Ser Ser Gln Gly Asn Gly Asn Val
  1               5                  10                  15

Phe Phe Ser Ser Leu Ser Ile Phe Thr Ala Leu Thr Leu Ile Arg Leu
             20                  25                  30

Gly Ala Arg Gly Asp Cys Ala Arg Gln Ile Asp Lys Ala Leu His Phe
         35                  40                  45

Asn Ile Pro Ser Arg Gln Gly Asn Ser Ser Asn Gln Pro Gly Leu
     50                  55                  60

Gln Tyr Gln Leu Lys Arg Val Leu Ala Asp Ile Asn Ser Ser His Lys
 65                  70                  75                  80

Asp Tyr Glu Leu Ser Ile Ala Thr Gly Val Phe Ala Glu Lys Val Tyr
                 85                  90                  95

Asp Phe His Lys Asn Tyr Ile Glu Cys Ala Glu Asn Leu Tyr Asn Ala
            100                 105                 110

Lys Val Glu Arg Val Asp Phe Thr Asn Asp Val Gln Asp Thr Arg Phe
        115                 120                 125

Lys Ile Asn Lys Trp Ile Glu Asn Glu Thr His Gly Lys Ile Lys Lys
    130                 135                 140

Val Leu Gly Asp Ser Ser Leu Ser Ser Ser Ala Val Met Val Leu Val
145                 150                 155                 160

Asn Ala Val Tyr Phe Lys Gly Lys Trp Lys Ser Ala Phe Thr Lys Thr
                165                 170                 175

Asp Thr Leu Ser Cys Arg Phe Arg Ser Pro Thr Cys Pro Gly Lys Val
            180                 185                 190

Val Asn Met Met His Gln Glu Arg Arg Phe Asn Leu Ser Thr Ile Gln
        195                 200                 205

Gln Pro Pro Met Gln Val Leu Glu Leu Gln Tyr His Gly Gly Ile Ser
    210                 215                 220

Met Tyr Ile Met Leu Pro Glu Asp Gly Leu Cys Glu Ile Glu Ser Lys
225                 230                 235                 240

Leu Ser Phe Gln Asn Leu Met Asp Trp Thr Asn Arg Arg Lys Met Lys
                245                 250                 255

Ser Gln Tyr Val Asn Val Phe Leu Pro Gln Phe Lys Ile Glu Lys Asn
            260                 265                 270

Tyr Glu Met Thr His His Leu Lys Ser Leu Gly Leu Lys Asp Ile Phe
        275                 280                 285

Asp Glu Ser Ser Ala Asp Leu Ser Gly Ile Ala Ser Gly Gly Arg Leu
    290                 295                 300

Tyr Val Ser Lys Leu Met His Lys Ser Phe Ile Glu Val Ser Glu Glu
305                 310                 315                 320

Gly Thr Glu Ala Thr Ala Ala Thr Glu Asn Asn Ile Val Glu Lys Gln
                325                 330                 335
```

```
Leu Pro Glu Ser Thr Val Phe Arg Ala Asp Arg Pro Phe Leu Phe Val
            340                 345                 350

Ile Lys Lys Asn Asp Ile Ile Leu Phe Thr Gly Lys Val Ser Cys Pro
        355                 360                 365

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:synthesis

<400> SEQUENCE: 7
tgtaaaacga cggccagt                                                       18

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:synthesis

<400> SEQUENCE: 8
accatgatta cgccaagctt g                                                   21

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence:synthesis

<400> SEQUENCE: 9
tcagagaggt cattc                                                          15

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:synthesis

<400> SEQUENCE: 10
tcattgatgg gtcctcaa                                                       18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:synthesis

<400> SEQUENCE: 11
agattcttga gctcagat                                                       18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:synthesis

<400> SEQUENCE: 12
aatggtggca taaacatg                                                       18
```

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:synthesis

<400> SEQUENCE: 13
acagacaaat tgaacttc                                                  18

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:synthesis

<400> SEQUENCE: 14
gaattcatgg cctcccttgc tgcagcaaa                                      29

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:synthesis

<400> SEQUENCE: 15
gtcgacttat caagggcaag aaactttgcc                                     30

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:synthesis

<400> SEQUENCE: 16
atgatctcag cattgtgaat g                                              21

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:synthesis

<400> SEQUENCE: 17
actgagggag ttgcttttct ac                                             22

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence:synthesis

<400> SEQUENCE: 18

Ser Asn Ile Val Glu Lys Gln Leu Pro Gln Ser Thr Leu Phe Arg
 1               5                  10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence:synthesis

```
<400> SEQUENCE: 19

Phe Arg Glu Met Asp Asp Asn Gln Gly Asn Gly Asn Val Phe Phe
 1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence:synthesis

<400> SEQUENCE: 20

Ser Gln Ser Gly Leu Gln Ser Gln Leu Lys Arg Val Phe Ser Asp
 1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence:synthesis

<400> SEQUENCE: 21

Ala Thr Gly Ser Asn Ile Val Glu Lys Gln Leu Pro Gln Ser Thr Leu
 1               5                   10                  15

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence:synthesis

<400> SEQUENCE: 22
atcggatcca tggcctccct tgctgcagca aatgcaga                            38

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence:synthesis

<400> SEQUENCE: 23
ataagctttc atcaagggca agaaactttg ccactgaata ag                       42

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence:synthesis
<220> FEATURE:
<221> NAME/KEY: misc_feature
<222> LOCATION: 26, 29
<223> OTHER INFORMATION: n is a or t or c or g.

<400> SEQUENCE: 24
gtgaatgctg tgtacttaaa ggcaantgn                                      29

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence:synthesis
```

```
<220> FEATURE:
<221> NAME/KEY: misc_feature
<222> LOCATION: 3, 9, 15
<223> OTHER INFORMATION: n is a or t or c or g.

<400> SEQUENCE: 25
aanagraang grtcngc                                                        17

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence:synthesis
<220> FEATURE:
<221> NAME/KEY: misc_feature
<222> LOCATION: 6, 9, 12, 15, 18, 21
<223> OTHER INFORMATION: n is a or t or c or g.

<400> SEQUENCE: 26
atggcntcng cngcngcngc naaygc                                              26

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence:synthesis

<400> SEQUENCE: 27
cgacctccag aggcaattcc agagagatca gccctgg                                  37

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence:synthesis

<400> SEQUENCE: 28
gtcttccaag cctacagatt tcaagtggct cctc                                     34

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence:synthesis

<400> SEQUENCE: 29
gctcagggca gtgaagatgc tcagggaaga                                          30

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence:synthesis

<400> SEQUENCE: 30
ctgacgtgca cagtcacctc gagcacc                                             27

<210> SEQ ID NO 31
<211> LENGTH: 36
<212> TYPE: DNA
<213> ORGANISM: Artificial Sequence
```

<220> FEATURE:
<223> OTHER INFORMATION: Description of Artificial Sequence:synthesis

<400> SEQUENCE: 31
gaggtctcag aagaaggcac tgaggcaact gctgcc                36

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence:synthesis

<400> SEQUENCE: 32
ctctatagga gacacttgg                19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence:synthesis

<400> SEQUENCE: 33
gaaacaaatc aaagcaaac                19

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence:synthesis

<400> SEQUENCE: 34
gaaattgaaa rcaarctgas yttycagaat                30

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence:synthesis

<400> SEQUENCE: 35
ctgasyttyc agaatctaat ggamtggac                29

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:synthesis

<400> SEQUENCE: 36
ggaytsaggr agtwgcttttt cwacratrtt                30

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence:synthesis

<400> SEQUENCE: 37
gaggtctcag aggagggcac tgaagccact gctgcc                36

```
<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence:synthesis

<400> SEQUENCE: 38
ccagtgcaga tctctctgga attgcctctg gaggtcgtc                              39

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence:synthesis

<400> SEQUENCE: 39
gcctgttact gtataggaaa ccaaaccg                                          28

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence:synthesis

<400> SEQUENCE: 40
atggcytccc tygctgcwgc raatgcagar tttkgc                                 36

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:synthesis

<400> SEQUENCE: 41
atcggatcca tggcctccct tgct                                              24

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence:synthesis

<400> SEQUENCE: 42
ataagctttc atcatcaagg gcaag                                             25

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence:synthesis

<400> SEQUENCE: 43
atggatccgc cgccatggcc tcccttgctg cagcaaatgc agag                        44

<210> SEQ ID NO 44
<211> LENGTH: 27
<212> TYPE: DNA
<213> ORGANISM: Artificial Sequence
```

```
<220> FEATURE:
<223> OTHER INFORMATION: Description of Artificial Sequence:synthesis

<400> SEQUENCE: 44
tatcctgagg cagtgttaac aagcaac                                          27
```